(12) United States Patent
Struve et al.

(10) Patent No.: US 8,478,375 B2
(45) Date of Patent: Jul. 2, 2013

(54) SENSOR FOR DETECTION OF CARBOHYDRATE

(75) Inventors: Casper Struve, Kongens Lyngby (DK); Jesper Svenning Kristensen, Virum (DK); Klaus Gregorius, Søborg (DK); Yihua Yu, Birkerød (DK)

(73) Assignee: Medtronic Minimed, Inc., Northridge, CA (US)

( * ) Notice: Subject to any disclaimer, the term of this patent is extended or adjusted under 35 U.S.C. 154(b) by 1524 days.

(21) Appl. No.: 11/792,046

(22) PCT Filed: Dec. 7, 2005

(86) PCT No.: PCT/EP2005/013115
§ 371 (c)(1),
(2), (4) Date: Feb. 28, 2008

(87) PCT Pub. No.: WO2006/061208
PCT Pub. Date: Jun. 15, 2006

(65) Prior Publication Data
US 2009/0131773 A1    May 21, 2009

(30) Foreign Application Priority Data
Dec. 7, 2004   (GB) .................................. 0426822.3

(51) Int. Cl.
*A61B 5/1455* (2006.01)
*C12Q 1/68* (2006.01)

(52) U.S. Cl.
USPC ........... 600/316; 422/68.1; 600/309; 600/310

(58) Field of Classification Search
USPC ....................... 600/309–344; 422/50, 62, 68.1
See application file for complete search history.

(56) References Cited

U.S. PATENT DOCUMENTS

| 4,330,299 | A | * | 5/1982 | Cerami ........................... 436/95 |
| 4,679,562 | A |   | 7/1987 | Luksha |
| 5,194,393 | A |   | 3/1993 | Hugl et al. |
| 5,277,872 | A |   | 1/1994 | Bankert et al. |
| 5,342,789 | A |   | 8/1994 | Chick et al. |
| 5,474,915 | A |   | 12/1995 | Dordick et al. |
| 5,476,776 | A |   | 12/1995 | Wilkins |

(Continued)

FOREIGN PATENT DOCUMENTS

EP  0 561 653 A1  9/1993
EP  0 594 772 B1  8/1996

(Continued)

OTHER PUBLICATIONS

Japanese Official Action and English translation in SN 2007-543805, dated Aug. 17, 2010.

(Continued)

*Primary Examiner* — Eric Winakur
*Assistant Examiner* — Marjan Fardanesh
(74) *Attorney, Agent, or Firm* — Nixon & Vanderhye PC

(57) ABSTRACT

A sensor for sensing analyte concentration comprises at least two different variants of an appropriate competitive binding assay, the sensor being capable of sensing accurately a required range of analyte concentrations by means of the variants of the assay each being capable of sensing accurately a part only of the required range of analyte concentrations and the variants of the assay being chosen to sense overlapping or adjoining ranges of concentration covering the whole of the required range.

24 Claims, 7 Drawing Sheets

U.S. PATENT DOCUMENTS

| | | | |
|---|---|---|---|
| 5,587,442 | A | 12/1996 | Kiessling et al. |
| 6,002,954 | A | 12/1999 | Van Antwerp et al. |
| 6,107,365 | A | 8/2000 | Bertozzi et al. |
| 6,232,130 | B1 | 5/2001 | Wolf |
| 6,256,522 | B1 | 7/2001 | Schultz |
| 6,271,315 | B1 | 8/2001 | Kiessling et al. |
| 6,383,220 | B1 | 5/2002 | Van Blitterswijk et al. |
| 6,538,072 | B2 | 3/2003 | Kiessling et al. |
| 6,671,527 | B2 | 12/2003 | Petersson et al. |
| 6,927,246 | B2 | 8/2005 | Noronha et al. |
| 7,045,361 | B2 | 5/2006 | Heiss et al. |
| 7,297,548 | B2 | 11/2007 | Kawanishi et al. |
| 2003/0125262 | A1 | 7/2003 | Kiessling et al. |
| 2003/0166136 | A1 | 9/2003 | Bandman et al. |
| 2003/0216300 | A1 | 11/2003 | Cantor et al. |
| 2004/0214190 | A1 | 10/2004 | Butz et al. |
| 2004/0248801 | A1 | 12/2004 | Kiessling et al. |
| 2004/0265898 | A1 | 12/2004 | Afar et al. |

FOREIGN PATENT DOCUMENTS

| | | |
|---|---|---|
| EP | 0 505 479 B1 | 9/2001 |
| EP | 1 247 522 A1 | 10/2002 |
| EP | 1 380 837 A1 | 1/2004 |
| JP | 2002-189027 | 7/2002 |
| JP | 2004-53363 | 2/2004 |
| JP | 2004-510527 | 4/2004 |
| WO | WO 91/09312 | 6/1991 |
| WO | WO 93/01498 | 1/1993 |
| WO | WO 97/19188 | 5/1997 |
| WO | WO 98/55869 | 12/1998 |
| WO | WO 00/02048 | 1/2000 |
| WO | 00/16099 | 3/2000 |
| WO | WO 00/16099 | 3/2000 |
| WO | WO 02/30275 A1 | 4/2002 |
| WO | WO 02/46752 A2 | 6/2002 |
| WO | WO 03/006992 A1 | 1/2003 |
| WO | WO 03/031578 | 4/2003 |
| WO | WO 2005/059037 A1 | 6/2005 |
| WO | WO 2005/110207 A1 | 11/2005 |

OTHER PUBLICATIONS

Hagberg, Journal of Applied Physiology, 1981, vol. 51, pp. 108.
International Search Report mailed Apr. 6, 2006.
Ballerstadt R. et al.: "Competitive-Binding Assay Method Based on Fluorescence Quenching Ofligands Held in Close Proximity by a Multivalent Receptor," Analytica Chimica Acta, Elsevier, Amsterdam, NL, vol. 345, No. 1-3, 1997, pp. 203-212, XP000901095.
K. Kataoka et al.: "Novel sensing system for glucose based on the complex formation between phenylborate and fluorescent diol compounds," J. Biochem., vol. 117, No. 6, 1995, pp. 1145-1147, XP008062001.
Lakowicz, Principles of Fluorescence Spectroscopy, Plenum Press, 1983, Chapter 3.
Tyagi et al, Nature Biotechnology (1998) 18:p49.
Russell et al, "Potentially Implantable Fluorescent Glucose Sensor . . . ", presented to American Institute of Chemical Engineers; 2000.
Kilpatrick (2002) Transfus. Med. 12, 335.
Teillet et al, Journal of Immunology, 2005, pp. 2870-2877.
Voss et al, Am. J. Respir. Cell Mol. Biol. vol. 4, pp. 88-94, 1991.
Cerdan et al, "Membranlektine von menschlichen . . . ", Parfumerie und Kosmetik, 74, Jahrgang, Nr. 3/93, pp. 164-180.
Chang et al, "Molecular Characterization of Human CD94: . . . ", Eur. J. Immunol. 1995, 25:2433-2437.
Kilpatrick et al, "P35, an opsonic lectin of the ficolin family . . . ", Immunology Letters 67 (1999) 109-112.
Itin et al, "ERGIC-53 Is a Functional Mannose-selective . . . ", Molecular Biology of the Cell, vol. 7, 483-493, Mar. 1996.
Christa et al, "High Expression of the human . . . ", Eur. J. Biochem. 267, 1665-1671 (2000).
Arce et al, "The Human C-type Lectin CLECSF8 . . . ", Eur. J. Immunol. 2004, 34:210-220.
Giorgino et al, "The sentrin-conjugating enzyme . . . ", PNAS, Feb. 1, 2000, vol. 93, No. 3, 1125-1130.
Appendices A, B and C of "Handbook of Animal Lectins: Properties and Biomedical Applications", Kilpatrick, Wiley 2000.
Kobayashi et al, 2004, J. Mag. Reson. Imaging, 20(3) 512-518.
Ballerstadt et al, Diabetes Technology & Therapeutics, vol. 6, No. 2, 2004.
Gestwicki et al (2002) Chemistry and Biology 9, p. 163.
Lakowicz, J.R., "Principles of Fluorescence Spectroscopy", $2^{nd}$ Edition, 1999.
Fakirov et al, Makromol. Chem. 191 (1990) 603-614.
Ballerstadt et al, "Competitive-binding assay method . . . ", Analytica Chimica Acta 345 (1997) 203-212.
Presanis et al, "Biochemistry and genetics of mannan-binding . . . ", Biochemical Society Transactions (2003), vol. 31, Part 4, pp. 748-752.
Gestwicki et al, J. Am. Chem. Soc., 2002, 124, 14922-14933.
Yang et al, "Synthesis of a multivalent display . . . ", Carbohydrate Research 337 (2002) 1605-1613.
Kanai et al, J. Am. Chem. Soc., 1997, 119, 9931-9932.
Lamanna et al, Journal of Bacteriology, Sep. 2002, p. 4981-4987.
Owen et al, Organic Letters 2002 vol. 4, No. 14, pp. 2293-22936.
Ehwald et al, "Viscosimetric Affinity Assay", Analytical Biochemistry 234, 1-8 (1996).
Beyer et al, "Compensation of Temperature and . . . ", Biotechnol. Prog. 2000, 16, 1119-1123.
Chinnayelka et al, "Resonance Energy Transfer . . . ", Biomacromolecules 2004, 5, 1657-1661.
Montalto et al, "A Keratin Peptide Inhibits . . . ", (2001), J. Immunol, 166, 4148-4153.
Pekari et al, "Synthesis of the Fully . . . ", J. Org. Chem. 2001, 66, 7432-7442.
Bahulekar et al, "Polyacrylamides containing sugar . . . ", Biotechnology Techniques, vol. 12(10) 1998 721-724.
Ballerstadt et al, "A homogeneous affinity . . . ", Sensors and Actuators B 38-39 (1997) 171-175.
Van Damme et al, Handbook of Plant Lectins: Properties and Biomedical Applications, Wiley & Sons, 1998, p. 142.

* cited by examiner

SENSOR FOR DETECTION OF CARBOHYDRATE

This application is the U.S. national phase of International Application No. PCT/EP2005/013115 filed 7 Dec. 2005 which designated the U.S. and claims priority to GB 0426822.3 filed 7 Dec. 2004, the entire contents of each of which are hereby incorporated by reference.

This invention relates to a sensor, to a method of preparing the sensor and to a method of using the sensor.

The sensor may be used in measuring the presence or concentration of an analyte, which may be a component of interstitial fluid, for example glucose.

The sensor is particularly suitable for use in situations in which glucose levels must be closely monitored and/or where glucose measurements must be taken repeatedly, such as in diabetes management.

In the management of diabetes, the regular measurement of glucose in the blood is essential in order to ensure correct insulin dosing. Furthermore, it has been demonstrated that in the long term care of the diabetic patient better control of the blood glucose levels can delay, if not prevent, the onset of retinopathy, circulatory problems and other degenerative diseases often associated with diabetes. Thus there is a need for reliable and accurate self-monitoring of blood glucose levels by diabetic patients.

It is desirable to measure blood glucose over the range of concentrations which may occur in a diabetic patient, that is, from 0 to 35 mM or even higher. While glucose is referred to extensively herein as a relevant example, it will be appreciated that the principles of the invention are widely applicable to a large range of analytes.

Currently, blood glucose is monitored by diabetic patients with the use of commercially available calorimetric test strips or electrochemical biosensors (e.g. enzyme electrodes), both of which require the regular use of a lancet-type instrument to withdraw a suitable amount of blood each time a measurement is made. On average, the majority of diabetic patients would use such instruments to take a measurement of blood glucose twice a day. However, the US National Institutes of Health has recommended that blood glucose testing should be carried out at least four times a day, a recommendation that has been endorsed by the American Diabetes Association. This increase in the frequency of blood glucose testing imposes a considerable burden on the diabetic patient, both in financial terms and in terms of pain and discomfort, particularly in the long-term diabetic who has to make regular use of a lancet to draw blood from the fingertips. Thus, there is clearly a need for a better long-term glucose monitoring system that does not involve drawing blood from the patient.

There have been a number of proposals for glucose measurement techniques that do not require blood to be withdrawn from the patient.

It has been observed that the concentration of analytes in subcutaneous fluid correlates with the concentration of said analytes in the blood, and consequently there have been several reports of the use of glucose monitoring devices which are sited in a subcutaneous location. The use of competitive binding assays for glucose which can be remotely interrogated is of particular interest.

A method of assaying a competitive binding is to use a proximity-based signal generating/modulating moiety pair (discussed in U.S. Pat. No. 6,232,120), which is typically an energy transfer donor-acceptor pair (comprising an energy donor moiety and an energy acceptor moiety). The energy donor moiety is photoluminescent (usually fluorescent).

In such methods, an energy transfer donor-acceptor pair is brought into contact with the sample (such as subcutaneous fluid) to be analyzed. The sample is then illuminated and the resultant emission detected. Either the energy donor moiety or the energy acceptor moiety of the donor-acceptor pair is bound to a receptor carrier, while the other part of the donor-acceptor pair (bound to a ligand carrier) and any analyte present compete for binding sites on the receptor carrier. Energy transfer occurs between the donors and the acceptors when they are brought together, which produces a detectable lifetime change (reduction) of the fluorescence of the energy donor moiety. Also, a proportion of the fluorescent signal emitted by the energy donor moiety is quenched.

The lifetime change is reduced or even eliminated by the competitive binding of the analyte. Thus, by measuring the apparent luminescence lifetime, for example, by phase-modulation fluorometry or time-resolved fluorometry (see Lakowicz, Principles of Fluorescence Spectroscopy, Plenum Press, 1983, Chapter 3), the amount of analyte in the sample can be determined.

It is to be noted that the efficiency of the energy transfer depends on the quantum yield of the donor, the overlapping of the emission spectrum of the donor with the absorption spectrum of the acceptor, and the relative distance and orientation between the donor and the acceptor.

In EP0561653 a method of interrogating a receptor and a ligand as described above, is disclosed.

An example of donor-acceptor energy transfer is fluorescence resonance energy transfer (Förster resonance energy transfer, FRET), which is non-radiative transfer of the excited-state energy from the initially excited donor (D) to an acceptor (A). The donor typically emits at shorter wavelengths, and its emission spectrum overlaps with the absorption spectrum of the acceptor. Energy transfer occurs without the appearance of a photon and is the result of long-range dipole-dipole interactions between the donor and acceptor.

The term resonance energy transfer (RET) is more correct because the FRET process does not involve the appearance of a photon. However, FRET and RET are often used interchangeably.

An important characteristic of FRET is that it occurs over distances comparable to the dimensions of biological macromolecules. The distance at which FRET is 50% efficient, called the Förster distance, is typically in the range of 20-60 Å. Förster distances ranging from 20 to 90 Å are convenient for competitive binding studies.

Labelling an analyte-binding moiety with a donor (D) and an analyte analogue with an acceptor (A), or vice versa, would create an assay capable of generating a measurable response based on the donor-to-acceptor distance. Thus, binding of the D-"analyte-binding moiety" to A-"analyte analogue" results in a decrease in donor intensity or lifetime. The analyte in the sample competes for the analyte-binding moieties on D-"analyte-binding moiety", releasing D-"analyte-binding moiety" from the acceptor (A). The intensity decay time and phase angles of the donor are thus expected to increase with increasing glucose concentration.

These principles have been used in glucose sensing by energy transfer.

WO91/09312 describes a subcutaneous method and device that employs an affinity assay based on glucose (incorporating an energy transfer donor-acceptor pair) that is interrogated remotely by optical means. Examples WO97/19188, WO00/02048, WO03/006992 and WO02/30275 each describe glucose sensing by energy transfer, which produce an optical signal that can be read remotely.

A person skilled in the art will appreciate that the acceptor could be a fluorophore. Any fluorescent signal emitted by the energy acceptor moiety following excitation with a beam of incident radiation at a wavelength within the absorption spectrum of the energy acceptor moiety is unaffected by the FRET process. It is therefore possible to use the intensity of the fluorescent signal emitted by the energy acceptor moiety as an internal reference signal, for example in continuous calibration of the sensor or to monitor the extent to which the sensor has degraded and thus indicate the need to implant or inject a fresh sensor. The fall of this signal below an acceptable baseline level would indicate the need to implant or inject a fresh sensor.

The energy acceptor moiety may, however, be a non-fluorescent dye. In this case a compound with fluorescence quenching capability is used instead of the specific energy acceptor moiety. An example of a powerful and non-specific fluorescence quencher is given by Tyagi et al. Nature Biotechnology (1998) 18: p49.

A limitation of the non-invasive assays for glucose levels in body fluids currently known is the range of glucose concentrations that the assay is able to measure accurately. The subcutaneous implant of WO91/09312 is said to be capable of measuring glucose concentrations in the range 0.5-18 mgml$^{-1}$ (2.6-94 mM), which covers all except the lower end of the target range necessary for intracellular fluid glucose concentration measurements. Accurate measurement at very low glucose concentrations is particularly important in diabetes control as it corresponds to hypoglycaemia.

A similar device is reported in WO98/05589, and is stated to have the ability to measure glucose concentrations in the range 0.05-5 mgml$^{-1}$ (0.26-26 mM), which covers the lower end of the range required for intracellular glucose concentration measurements.

A third device is disclosed in WO00/16099.

The above devices use competition assays which comprise an analyte analogue, and a binding agent which is capable of competitively binding the analyte of interest and the analyte analogue.

The ability of the analyte to displace the analyte from the binding agent is dependent upon the identities of the analyte, ligand and binding agent. The measurable response produced by the assay is correlated with the proportion of the analyte bound to the binding agent.

For a particular assay, therefore, there will be a range of concentrations of analyte that may be measured. This range will be defined by a minimum concentration of analyte required to displace the analyte analogue from the binding agent, and a maximum concentration of analyte at the point at which all of the analyte analogue has been displaced from the binding agent.

The tailoring of one assay to produce a measurable response over all of the analyte concentration range of interest, particularly when there are other properties of the assay (e.g. longevity, cost, toxicity) which must be taken into account, is a difficult and potentially expensive process.

The inventors have found a means to overcome the limitation of the concentration range over which the assay is accurate.

Accordingly, in a first aspect, the present invention provides a sensor for sensing analyte concentration which comprises at least two different variants of an appropriate competitive binding assay, the sensor being capable of sensing accurately a required range of analyte concentrations by means of the variants of the assay each being capable of sensing accurately a smaller range of analyte concentrations and the variants of the assay being chosen to sense overlapping or adjoining ranges of concentration covering the whole of the required range.

Suitably, the variants of the assay have optimum sensitivity within the range of analyte concentrations which they are capable of sensing accurately.

Preferably, the sensor is capable of sensing analyte concentration over a wider range of concentrations than that over which any single assay variant is capable of sensing concentration.

The assay variants may be capable of sensing analyte concentration over concentration ranges which are similar or different in width, and similar or different in IC$_{50}$ value. The use of a combination of assay variants capable of sensing analyte concentration over concentration ranges which are different in width is particularly useful as it allows certain parts of an overall concentration range to be monitored more closely (see below).

Preferably, the sensor is suitable for the detection or measurement of analyte in body fluid, for example subcutaneous fluid. It is desirable for the sensor to be suitable for use in vivo, and this is discussed in more detail below.

Preferably, the analyte to be detected or measured by the assays is a carbohydrate, more preferably a monosaccharide, and highly preferably glucose.

Preferably, the sensor is capable of measuring blood glucose for concentrations over at least part of the range of 0 to 35 mM glucose, for example over the range of 0 to 25 mM glucose. For example, one assay variant may have an IC$_{50}$ value of 7-8 mM and another assay variant may have an IC$_{50}$ value of about 18 mM. More preferably, the sensor is capable of measuring glucose concentrations over the range of 2 to 10 mM glucose. A dosage-response curve which is as close as possible to linear within this range is desirable.

In a preferred embodiment, the sensor comprises two variants of a competitive binding assay, one variant being capable of sensing glucose concentrations in the range 0-15 mM, and the other variant being capable of sensing glucose concentrations in the range 10-35 mm, 10-25 mM or 15-35 mM.

The use of overlapping ranges is preferred as each assay variant has optimum sensitivity around the IC$_{50}$ value. For example, the inventors have prepared a single assay with a response for glucose in the range 0-100 mM of 7.5 phase degrees corresponding to 0.08° pr. mM Glc. If two variants of the appropriate competitive binding assay were to be used optimally, 7.5 phase degrees would be available in the range of 0-15 mM Glc corresponding to 0.5° pr. mM Glc, and in the other assay 7.5 phase degrees would be available in the range of 10-25 mM Glc corresponding to 0.5° pr. mM Glc.

A combination of an assay variant capable of sensing glucose concentrations in the range 0-35 mM glucose with an assay variant capable of sensing glucose concentrations in the narrower range 0-10 mM glucose is particularly preferable, since a more sensitive assay in the range 0-10 mM glucose would reduce the number of false hypoglycaemic alarms, often associated with other continuous glucose monitoring devices.

Preferably, the sensor further comprises a third variant of the competitive binding assay, capable of sensing glucose concentrations in the range of 15-40 mM or 25-50 mM.

In a preferred embodiment, the present invention makes use of a competitive assay wherein an analyte analogue may bind non-covalently to the analyte binding agent at a number of sites. The bonds are typically formed at analyte analogue moieties of the analyte analogue. The concentration of analyte required to displace the analyte analogue will depend on the avidity (overall binding ability) of the analyte analogue for the analyte binding agent.

The parameters which affect avidity of an analyte analogue for a given analyte binding agent include:
  number of analyte analogue moieties;
  affinity (individual binding ability) of the analogue analyte moieties for the lectin;
  calcium concentration; and
  flexibility of the analyte analogue.

Physiological calcium concentration cannot be controlled. However, the other parameters can be selected.

The greater the number of analyte analogue moieties having a given affinity, the greater the avidity of the ligand for the analyte binding agent, and the greater the concentration of the analyte required to displace it.

Similarly, the higher the affinity of a given number of analyte analogue moieties, the greater the avidity of the ligand for the analyte binding agent, and the greater the concentration of the analyte required to displace it.

Therefore, the concentration range which can be sensed by an assay variant can be changed between higher and lower analyte concentrations by varying the number of analyte analogue moieties, the nature of some or all of the analyte analogue moieties and the flexibility of the analyte analogue.

A combination of assay variants, each containing an analyte analogue having a different avidity for the analyte binding agent, may therefore be used, the assay variants being chosen such that the ranges of the individual assay variants overlap or adjoin and, when put together, cover the whole range of analyte concentrations of interest.

Thus, in a preferred embodiment, the competitive binding assays each comprise:
  an analyte binding agent; and
  an analyte analogue comprising at least one analyte analogue moiety;
  wherein the analyte binding agent binds the at least one analyte analogue moiety of the analyte analogue to form a complex from which the analyte analogue is displaceable by said analyte, and wherein the different assays are distinguished by the number or nature of the analyte analogue moieties comprised by the analyte analogue.

The skilled person will appreciate that the assay variants could differ in ways other than having different analyte analogues. For example, different analyte binding agents could be used.

Detection

Preferably, the assay variants produce a measurable optical signal which can be correlated with analyte concentration, e.g. upon stimulation with optical energy producing fluorescence.

Suitable detection techniques include FRET, fluorescence energy transfer, fluorescence polarisation, fluorescence quenching, phosphorescence, luminescence enhancement, luminescence quenching, diffraction or plasmon resonance.

The binding assay generating the optical signal should preferably be reversible such that a continuous monitoring of fluctuating levels of analyte can be achieved. This reversibility is a particular advantage of the use of a binding assay format in which the components of the assay are not consumed.

Preferably, the detectable or measurable optical signal is generated using a proximity based signal generating/modulating moiety pair; A signal is generated or modulated when a first member of the pair is brought into close proximity with a second member of the pair.

In a preferred embodiment, the analyte binding agent is labelled with one of a proximity based signal generating/modulating moiety pair and the analyte analogue is labelled with the other of the proximity based signal generating/modulating moiety pair, and there is a detectable difference in signal when the analyte analogue and analyte binding agent form the complex and when the analyte analogue is displaced by the analyte from the complex.

Preferably, the proximity based signal generating/modulating moiety pair is an energy donor moiety and energy acceptor moiety pair. Energy donor moieties and energy acceptor moieties are also referred to as donor and acceptor chromophores (or light absorbing materials) respectively. An energy acceptor which does not emit fluorescence is referred to as a quenching moiety.

In this case, the lectin is labelled with one of an energy donor and energy acceptor moiety pair and the analyte analogue is labelled with the other of the energy donor and energy acceptor moiety pair. The detectable difference in signal corresponds to a detectable difference in energy transfer from the energy donor moiety to the energy acceptor moiety.

More preferably, the analyte analogue bears the energy acceptor moiety and the analyte binding agent bears the energy donor moiety.

Suitably, the sensor of the invention incorporates an assay which generates an optical readout using the technique of FRET.

In a preferred embodiment, the variants of the competitive binding assay each comprise:
  an analyte binding agent labelled with a first light-absorbing material;
  a macromolecule labelled with a second light-absorbing material and comprising at least one analyte analogue moiety;
  wherein the analyte binding agent binds said at least one analyte analogue moiety of the macromolecule to form a complex from which said macromolecule is displaceable by said analyte, and wherein said complex is able to absorb light energy and said absorbed light energy is able to be non-radiatively transferred between one of the light-absorbing materials and the other of the light-absorbing materials with a consequent measurable change in a fluorescence property of said light absorbing materials when present in said complex as compared to their said fluorescence property when said macromolecule is displaced by said analyte from said complex, and wherein the different variants of the assay are distinguished by the number of analyte analogue moieties present in the macromolecule.

Fluorescence lifetime or fluorescence intensity measurements may be made. Fluorescence lifetime may be measured by phase modulation techniques.

Where the assay is to be used in vivo, it is desirable for donors to fluoresce at 550 to around 700 nm and for acceptors to absorb light at around 650 nm. This avoids overlap between the donor fluorescence and in vivo autofluorescence at lower wavelengths.

Alexa Fluor 594™ (e.g. as succinimidyl ester) is an energy donor moiety with a suitable emission spectrum for use in vivo. This dye absorbs at 594 nm and fluoresces at 620 nm.

The HMCV dyes described in WO05/059037 are suitable energy acceptor moieties for use in the invention. These dyes are stabilised carbenium ions. An example is Hexa-Methoxy-Crystal Violet succinimidyl ester (HMCV-1).

Alternatively, QSY 21™ may be used as an energy acceptor moiety with Alexa Fluor 594™ as an energy donor moiety.

Fluorescence lifetime or fluorescence intensity measurements may be made. Fluorescence lifetime may be measured by phase modulation techniques (discussed below).

In a preferred embodiment, the analyte binding agent is labelled with Alexa Fluor 594™ as energy donor moiety, the analyte analogue is labelled with HMCV-1 as energy acceptor moiety, and fluorescence lifetime is measured by phase modulation techniques.

In assays of this type, the material retaining the assay components preferably provides sufficient space for the energy donor and the energy acceptor moieties to separate when not bound to one another so that energy transfer can cease.

Analyte Binding Agent

Preferably, the analyte binding agent is a lectin. The term "lectin" includes any carbohydrate-binding protein not obviously involved in carbohydrate metabolism and which does not belong to any of the major classes of immunoglobulins. Lectins show selective binding to carbohydrates via carbohydrate recognition domains (CRDs). Lectins occur naturally in both monomeric and multimeric forms, the latter often comprising a number of subunits, each bearing several CRDs. The use of a lectin analyte binding agent is therefore particularly suitable when the analyte is a carbohydrate.

The FRET-based systems discussed above rely on Concanavalin A (Con A) as the glucose binding agent. Concanavalin A is a plant derived lectin.

Concanavalin A is not stable for long periods under assay conditions (see concurrently filed application claiming priority from GB0426823.1).

Also, Concanavalin A is toxic and potentially immunogenic (however, it is used in glucose assays in small quantities which are thought to be safe in the human body).

Our co-pending application referred to above is based on the appreciation that there is a need to find glucose binding moieties which do not have the disadvantages associated with Con A. The use of alternative glucose binding moieties has been investigated and surprisingly, it has been found that animal lectins, in particular human lectins, can be used as glucose binding moieties.

Preferably, therefore, the lectin is an animal lectin, although the use of plant lectins such as Con A is not excluded.

Preferably, the lectin is a C-type (calcium dependent) lectin.

Preferably, the animal lectin is a vertebrate lectin, for example a mammalian lectin, more preferably a human or humanised lectin. However, it may alternatively be a bird lectin, fish lectin or an invertebrate lectin such as an insect lectin.

Suitably, the lectin is a human lectin derived from the human body. Alternatively, the lectin may be a recombinantly manufactured lectin.

As a further alternative, the lectin may be a humanised animal lectin, for example a humanised bovine lectin. This applies where there is a corresponding human lectin. The lectin may be humanised in an analogous way to antibodies.

Suitably, the lectin is in multimeric form. Multimeric lectins may be derived from the human or animal body. Alternatively, the lectin may be in monomeric form. Monomeric lectins may be formed by recombinant methods or by disrupting the binding between sub-units in a natural multimeric lectin derived from the human or animal body. Examples of this are described in U.S. Pat. No. 6,232,130.

Preferably, the lectin has three or more CRDs. More preferably, the lectin has 6, 9, 12 15 or more CRDs.

Preferably, the lectin is a collectin (collagen-like lectin). These are C-type animal lectins which have collagen like sequences (Gly-Xaa-Yaa triplet). MBL is a C-type collectin whereas Concanavalin A is a C-type lectin. Monomeric collectin CRDs can be prepared by the action of collagenase.

Preferably, the lectin is mannose binding lectin, conglutinin or collectin-43 (e.g. bovine CL-43) (all serum collectins) or a pulmonary surfactant protein (lung collectins).

Mannose binding lectin (also called mannan binding lectin or mannan binding protein, MBL, MBP), for example human MBL, has proved particularly interesting. MBL is a collagen-like defence molecule which comprises several (typically 3 to 4 (MALDI-MS), though distributions of 1 to 6 are likely to occur (SDS-PAGE).) sub-units in a "bouquet" arrangement, each composed of three identical polypeptides. Each sub-unit has a molecular weight of around 75 kDa, and can be optionally complexed with one or more MBL associated serine proteases (MASPs). Each polypeptide contains a CRD. Thus, each sub-unit presents three carbohydrate binding sites. Trimeric MBL and tetrameric MBL (which are the major forms present in human serum, Teillet et al., Journal of Immunology, 2005, page 2870-2877) present nine and twelve carbohydrate binding sites respectively.

MBL occurs naturally in the body as part of the innate immune system where it binds mannose moieties coating the surface of bacteria. Human MBL is not toxic and is non-immunogenic to humans. MBL of other species is expected to be immunogenic but not toxic to humans.

Human MBL is commercially available both in a form derived from the human body and in a recombinantly manufactured form. It is used as a replacement therapy in the treatment of MBL deficient patients who are believed to have increased susceptibility to infectious diseases.

Suitably, the lectin is MBL substantially in trimeric and/or tetrameric form. As explained above, trimeric MBL and tetrameric MBL are believed to be the major naturally occurring multimeric forms in human serum.

Alternatively, the lectin may be a pulmonary surfactant protein selected from SP-A and SP-D. These proteins are similar to MBL. They are water-soluble collectins which act as calcium dependent carbohydrate binding proteins in innate host-defence functions. SP-D also binds lipids. SP-A has a "bouquet" structure similar to that of MBL (Kilpatrick, D. C. (2000) Handbook of Animal Lectins, p37, J Appl Physiol 51, 1-8, Am J Respir Cell Nol Biol 4, 88-94). SP-D has a tetrameric "X" structure with CRDs at each end of the "X".

Other suitable animal lectins are those set out in the following list:

PC-lectin (US 20030216300, US 20040265898)
CTL-1 (US 179528/10)
Keratinocyte membrane lectins (Parfuemerie und Kosmetik 74, 164-80)
CD94 (Eur J Immunol 25, 2433-7)
P35 (synonym: human L-ficolin, a group of lectins) (Immunol Lett 67, 109-12)
ERGIC-53 (synonym: MR60) (Mol Biol Cell, 7, 483-93)
HIP/PAP (Eur J Biochem 267, 1665-71)
CLECSF8 (Eur J Immunol 34, 210-20)
DCL (group of lectins) (Appl no 00231996/US)
GLUT family proteins, especially GLUT1, GLUT4 and GLUT11 (PNAS 97, 1125-30)

Further suitable animal lectins are set out in Appendices A, B and C of "Handbook of Animal Lectins: Properties and Biomedical Applications", David C. Kilpatrick, Wiley 2000.

As discussed above, different analyte binding agents may be used in different assay variants.

Teillet et al. (J. Immunol., 2005, p2870-2877) demonstrates that trimeric (9 CRDS) MBL binds less strongly to carbohydrate than tetrameric (12 CRDS) MBL. Using an assay with different lectins or as the case here different MBL multimers can alter be used to alter sensitivity as well.

Therefore, the different assay variants may be distinguished by having different lectin analyte binding agents. Preferably, the different lectin analyte binding agents are different MBL species, for example MBL species having different numbers of CRDs (for example 9 CRDs and 12 CRDs as discussed above).

The analyte binding agent is preferably labelled as discussed above.

Analyte Analogue

Preferably, the analyte analogue is a glucose analogue.

Preferably, the analyte analogue comprises a plurality of carbohydrate or carbohydrate mimetic analyte analogue moieties which bind to binding sites of the analyte binding agent. The term "carbohydrate" includes sugars.

Suitable carbohydrate mimetic moieties include peptides such as keratin peptide (SFGSGFGGGY) which mimics N-acetyl glucosamine. It has been shown that keratin peptide can inhibit MBL (Mantacto et al. 2001 J. Immunol. 166, 4148-4153).

Suitably, the carbohydrate analyte analogue moieties are monosaccharides or oligosaccharides (oligomers). The analyte analogue itself may be an oligosaccharide (see below).

Suitable monosaccharides are optionally derivatised tetroses, pentoses, hexoses, heptoses or higher homologous aldoses or ketoses, for example optionally derivatised D-glucose, D-mannose, N-acetyl-D-glucosamine, L-fucose, D-fructose, D-tagatose or D-sorbitol.

Suitable oligomers may be linear or branched homooligomers or mixed oligomers, for example containing from 2 to 50 carbohydrate units.

The preferred glycosylation is 1→6 or 1→2, as 1→3 and 1→4 glycosylation is expected to interrupt MBL binding. For example, nona(1→6)-α-glucose (dextran 1500 Da) is expected to have higher avidity for MBL than 1,3-β-D-glucoses (e.g. laminanarihexaose). Suitable oligosaccharides include pannose, maltose, maltotriose, isomaltotriose, D-leucrose, erlose, D-palatinose, D-turanose or 1 to 250 kDa dextran (preferably 1 to 40 kDa dextran, for example 1 kda, 1.5 kDa, 5 kDa, 6 kDa, 10 kDa, 12 kDa, 20 kDa, 25 kDa or 40 kDa dextran).

Preferably, the analyte analogue moieties of at least one assay variant are selected from D-fructose, D-leucrose, N-acetyl-glucosamine, D-mannose, L-fucose, N-acetyl-mannosamine, D-arabinose, myo-inositol, D-tagatose, erlose, D-glucose, D-palatinose, D-turanose, D-ribose, D-sorbitol.

Examples of a synthetic branched saccharide are dendrimer "wedges" used to construct dendrimers (e.g. TRIS derived trisaccharide with an amine linker, shown below). Such "wedges" could be conjugated onto a protein such as HSA (human serum albumin), for example via a bifunctional amine linker.

It has been found by the inventors that the affinity of common carbohydrate moieties for MBL is as follows: D-Mannose, N-acetyl-D-mannosamine, D-fructose, D-leucrose, erlose, N-acetyl-D-glucosamine, L-Fucose>myo-inositol, D-glucose, D-arabinose, D-palatinose, D-turanose, D-sorbitol, D-ribose, D-tagatose>D-lyxose>lactose, L-arabinose, D-galactose.

The skilled person will appreciate that using this list variant assays could be chosen wherein the analyte analogues comprise analyte analogue moieties of different affinities for the analyte binding agent. For example, an analyte analogue with mannose analyte analogue moieties would have higher avidity for MBL as analyte binding agent than an analyte analogue with the same number of glucose analyte analogue moieties. Therefore, the mannose containing analyte analogue would require more glucose analyte to be displaced from MBL, and this assay would have optimum sensitivity over a higher glucose concentration range than the assay using the glucose containing analyte analogues.

The skilled person will also appreciate that an analyte analogue comprising more than one type of analyte analogue moiety could be prepared. This allows greater control over the optimum glucose sensitivity ranges.

Preferably, the analyte analogue moieties of at least one assay variant comprise at least one glucose moiety and/or at least one N-acetyl glucosamine moiety and/or at least one mannose moiety, since these have a high affinity for MBL and other animal lectins. Most preferably, the analyte analogue moieties of at least one assay variant are D-glucose.

Preferably, the analyte analogue comprises a macromolecule.

Preferably, the macromolecule is a natural polymer. More preferably, the macromolecule is linear.

Three different types of structure for the analyte analogue are of particular interest.

First, the analyte analogue may be a carbohydrate-protein conjugate or a carbohydrate-dendrimer conjugate, so that the macromolecule is a protein or a dendrimer. In either of these cases, carbohydrate mimetic moieties may be used instead of or in addition to carbohydrate moieties as analyte analogue moieties.

Preferred proteins for use in the conjugate are human proteins having a molecular weight of at least 10 kDa, preferably at least 20 kDa. Preferably, the protein has a non-globular overall tertiary structure. It is believed that this assists binding at more than one binding site, leading to high avidity. Monoclonal antibodies such as herceptin and Remicade™ (an immunoglobulin having several globular domains with a non-globular "Y"-shaped overall tertiary structure) are suitable. Other alternative suitable proteins are human thrombin, human lactoferrin and Factor XIII.

As another example of a carbohydrate-protein conjugate, the protein may be a lectin-derived protein, for example a lectin with the CRDs removed.

Suitably, the conjugate may be a carbohydrate-albumin conjugate. For example, the conjugate may be a mannose-HSA conjugate or a mannose-BSA (bovine serum albumin) conjugate. However, conjugates of this type are not preferred since, as mentioned above, binding to MBL has been found to be dependent on calcium concentration. At physiological calcium concentrations a 70 kDa mannose-HSA conjugate with 20 mannose residues was found not to bind MBL. The dependence on calcium concentration decreases with increasing mannosylation.

The skilled person would be aware of synthetic routes to conjugates of this type. As an example, N-isothiocyanato-4-aminophenyl-O-α-D-mannopyranoside (Man-ITC) can be conjugated onto HSA.

In a preferred embodiment, in each competitive binding assay variant the macromolecule is HSA and the analyte analogue moiety is glucose or mannose, and each variant of the competitive binding assay contains an HSA-glucose or mannose conjugate comprising a different number of glucose or mannose moieties. Suitably in this embodiment the analyte binding agent is MBL.

Dendrimers for use in the invention preferably have amine-functionalised, carboxylic acid-functionalised or hydroxyl-functionalised surfaces. Preferably, the dendrimers are of the polyamidoamine (PAMAM) or polypropylenimine (DAB) type. Preferably, the molecular weight is less than 60 kDa, for example around 2 to 10 kDa. Such dendrimers can be cleared by the kidney (Kobayashi et al., 2004, J. Mag. Reson. Imaging 20(3) 512-518).

Second, the analyte analogue may be an optionally derivatised polymer of carbohydrate and/or carbohydrate mimetic moieties (both included in the term "mpolysaccharide" used herein). Dextran (a glucose polymer, poly(1→6)-α-glucose) binds strongly to MBL and similar lectins. The inventors believe that this is a result of the large number of glucose residues (approximately 430 residues in 70 kDa dextran) and the flexibility of dextran. The concentration of glucose needed to displace dextran from MBL is therefore high.

A glucose assay variant based on dextran and MBL can optimally measure glucose concentrations of around 30 mM. This is much higher than the normal 5 mM glucose concentration in blood. Such an assay variant can measure glucose concentrations from 0 to 10 mM with a sensitivity of only about one third of the total phase response.

The present inventors therefore looked for alternative analyte analogues which would bind MBL and similar lectins less strongly, so that an assay variant could be obtained with more than one third of the total phase response would be available in the 0 to 10 mM glucose range.

The inventors discovered that treating dextran with periodate (which oxidatively cleaves the glucose pyranose ring between the 2 and 3 or 3 and 4 carbons to form a dialdehyde) can be used to reduce the avidity of dextran for MBL and similar lectins. This appears to be because MBL binds to the 3 and 4 equatorial hydroxyls of glucose as explained above. The 3 and 4 hydroxyl groups could inactivated in other ways (for example by oxidation, reduction, alkylation, substitution, glycosylation or esterification).

Very surprisingly, the inventors found that periodate treated dextran-MBL binding is not prevented by physiological calcium concentrations. This is in contrast to mannose-HSA conjugate MBL binding as discussed above. It would have been expected that periodate-treated dextran MBL binding was prevented by physiological calcium concentrations, particularly since the glucose moieties of dextran have lower affinity for MBL than do mannose moieties.

Theoretically two equivalents of periodate per glucose unit could be consumed (one per diol). However, it has been found that 1 to 100 equivalents of periodate is suitable for 70 kDa dextran.

Treatment of the dialdehyde with ammonia or an amine followed by reduction (e.g. with sodium cyanoborohydride) can be used to give an aminated dextran. A procedure can also be used in which the dialdehyde is aminated followed by optional catalytic hydrogenation to yield the free amine. Benzylamine is a useful amine in this context. A benzylamine derived aminated dextran can be used to assess the degree of periodate cleavage using spectrophotometric techniques. If the benzyl group is removed by catalytic hydrogenation, energy donor or energy acceptor moieties can be coupled to the remaining amine.

Alternatively, as discussed above, polysaccharide-based analyte analogues can be synthesised which bear different carbohydrate or carbohydrate mimetic analyte analogue moieties of different affinity for MBL and similar lectins. Derivatisation of dextran with mannose moieties to adjust the glucose detection range in a Concanavalin A FRET assay is disclosed in Ballerstadt et al., Diabetes Technology & Therapeutics, vol. 6, no. 2, 2004.

Galactose binds to MBL with very low affinity. Therefore, an analyte analogue containing galactose moieties (for example galactose-derivatised dextran) has lower avidity for MBL than the underivatised analyte analogue.

N-acetyl-glucosamine has a high affinity for MBL. Therefore, an analyte analogue containing N-acetyl-glucosamine moieties (for example GlcNAc derivatised amylose) would have higher avidity for MBL than the underivatised analyte analogue.

Preferably in this embodiment, the analyte analogue is selected from optionally derivatised dextran, mannan, amylose, amylopectin, glycogen, hyaluronate, chondroitin, heparin, dextrin, inulin, xylan, fructan and chitin. As galactose has very low affinity for MBL, a non-derivatised polymer of galactose such as agarose is not preferred as an analyte analogue.

The skilled person would be aware of ways in which a polysaccharide can be derivatised with carbohydrate moieties. As an example, amine-functionalised polysaccharides (for example aminodextran, which is commercially available from CarboMer, San Diego, Calif., USA, Cat. No. 5-00060 or Molecular Probes, Eugene, Oreg., USA, Cat No. D1862) or the aminated dextrans referred to above may conveniently be derivatised. Alternatively, alcohol groups in the polysaccharide and amine groups in the carbohydrate or carbohydrate mimetic moieties may be linked using divinylsulphone. Methods of derivatising dextran are disclosed in EP594772.

Examples of suitable carbohydrate analyte analogue moieties for derivatisation of polysaccharides are those set out in connection with carbohydrate-protein and carbohydrate-dendrimer conjugates above.

In a preferred embodiment, the analyte is glucose, and in each variant of the competitive binding assay the macromolecule and analyte analogue moiety together form a derivatised dextran, and each variant of the competitive binding assay contains a dextran derivatised such that the number of analyte analogue moieties incorporated into the dextran is different. Suitably in this embodiment the analyte binding agent is MBL.

In a particularly preferred embodiment, the derivatised dextran in each case is optionally periodate-treated dextran.

Third, the analyte analogue may be a synthetic polymer.

Synthesis of an artificial polymer rather than derivatisation of a protein or polysaccharide allows the parameters of the polymer (for example molecular flexibility, water solubility, molecular weight, nature of carbohydrate or carbohydrate mimetic moieties, number of carbohydrate or carbohydrate mimetics moieties, number of proximity based signal generating/modulating moieties) to be readily controlled to improve assay performance and to provide suitable assay variants. Compared with a polysaccharide, a synthetic polymer has the advantage that the number of carbohydrate analyte analogue moieties can be controlled independently of the length of the polymer. Furthermore, using non-ring containing monomers such as 2-hydroxyethyl acrylate (HEA) in the polymer gives increased molecular rotational flexibility compared with dextran.

Without wishing to be bound by this theory, the inventors believe that it is important that proximity based signal generating/modulating moieties are close to the binding moiety to generate a strong signal. Globular ligands concentrate binding moieties and proximity based signal generating/modulating moieties on a spherical surface so that they are close. In dextran, which is linear, the backbone consists of binding moieties, and consequently it is not possible to control whether binding is close to or remote from an proximity based signal generating/modulating moiety. This can be controlled in the synthetic polymer by positioning the binding moieties close to the proximity based signal generating/modulating moieties.

Preferably in this embodiment, the analyte analogue is a non-saccharide flexible water-soluble polymer bearing pendant carbohydrate or carbohydrate mimetic analyte analogue moieties.

The term "flexible" includes polymers which are capable of significant intermonomeric rotation. Preferably, the polymers do not contain bulky groups (for example ring structures, tert-butyl groups or other sterically large groups) other than the pendant carbohydrate or carbohydrate mimetic analyte analogue moieties and proximity based signal generating/modulating moieties (discussed below). Preferably, such polymers have very few double bonds in the backbone structure (for example less than 10%). Suitably, such polymers do not have a globular tertiary structure, although they may have such a structure.

Preferably, the polymer is unbranched (unlike the dendrimers discussed above). This improves flexibility of the polymer. However, the polymer may be branched or cross-linked to some extent provided that this does not lead to formation of a hydrogel. For example, 1 to 5 branchings in a polymer with an overall molecular weight of 100 kDa is acceptable.

The term "water soluble" includes polymers having a water solubility at room temperature of at least 4 mg/ml, preferably at least 25 mg/ml, more preferably at least 50 mg/ml, for example at least 100 mg/ml. The solubility will be higher at body temperature. It is important that the polymer is water soluble so that it will dissolve in interstitial fluid when used in a sensor in the body as discussed below. The polymer should be water soluble even when bound to a carbohydrate binding molecule such as MBL.

Preferably, the polymer includes no more than 1 to 5 types of monomer unit, more preferably no more than 3 monomer units.

Suitably, the polymer is a co-polymer comprising first monomer unit residues bearing pendant carbohydrate or carbohydrate mimetic moieties and second monomer unit residues bearing pendant proximity based signal generating/modulating moieties. Alternatively or additionally, a single type of monomer unit residue bearing both pendant carbohydrate or carbohydrate mimetic moieties and pendant proximity based signal generating/modulating moieties may be used. The use of first and second monomer units is preferred, since the amounts of carbohydrate or carbohydrate mimetic moieties and proximity based signal generating/modulating moieties can then be controlled independently.

Preferably, the co-polymer is a random co-polymer. However, it may also be an alternating co-polymer. Use of a block co-polymer with large blocks is not preferred. However, a block co-polymer with blocks of low molecular weight (for example 1 to 3 kDa) may be used.

Preferably, when used in an assay with MBL as a carbohydrate binding molecule, the polymer binds to MBL at 0 mM glucose at least 50% as strongly as aminodextran, more preferably at least as strongly as aminodextran, but is more easily inhibited. It is particularly important that the polymer is easily inhibited over the range of 0 to 35 mM glucose, and especially over the range of 2 to 15 mM. This provides an assay over glucose concentrations of particular physiological interest which is more sensitive than a similar assay using aminodextran as a glucose analogue.

More than one type of monomer unit residue bearing carbohydrate or carbohydrate mimetic moieties may be present. The carbohydrate or carbohydrate mimetic moieties may be different, with different affinities for MBL and similar lectins.

Suitably, the first monomer units (or single monomer units) are each a double bond-containing derivative of a carbohydrate or carbohydrate mimetic moiety. However, the first monomer units (or single monomer units) may each be a double bond-containing molecule containing a functional group to which the carbohydrate or carbohydrate mimetic moiety can be linked, suitably after polymerisation.

Preferably, the double bond-containing derivative of the carbohydrate or carbohydrate mimetic moiety is an allyl or vinyl containing derivative of a carbohydrate or carbohydrate mimetic moiety. Other suitable double bond-containing derivatives of carbohydrate or carbohydrate mimetic moieties include homologues of allyl derivatives, for example 3-butenyl or 4-pentenyl derivatives, or styrene derivatives with the carbohydrate or carbohydrate mimetic moiety at the 4 position. Further suitable double bond-containing derivatives of carbohydrate or carbohydrate mimetic moieties include HEA, 2-hydroxyethyl methacrylate (HEMA) or vinyl alcohol (VA) based derivatives.

The carbohydrate or carbohydrate mimetic moieties may be linked to amine, acid, alcohol and/or sulphone functional groups of the first monomer units (or single monomer units). For example, alcohol groups in the monomer units and amine groups in the carbohydrate or carbohydrate mimetic moieties may be linked using divinylsulphone. Where the carbohydrate is mannose, the linkage should not be via the C3-OH or C4-OH groups, since these are important in binding to MBL. In this case, divinylsulphone linkage may be inappropriate.

Amino derivatised carbohydrate moieties can be produced by reductive amination of disaccharides. This allows the carbohydrate moiety to be linked at its anomeric position (C1).

The carbohydrate or carbohydrate mimetic moiety could be connected to alcohol groups (e.g. in HEA) by Fischer glycosidation.

It is not necessary for the first monomer units (or single monomer units) to contain double bonds.

Examples of suitable carbohydrates for use in the co-polymer are as discussed in connection with Carbohydrate-Protein Conjugates above.

Suitably, the second monomer units (or single monomer units) are each a double bond-containing molecule containing a functional group to which the proximity based signal generating/modulating moiety can be linked, suitably after polymerisation. Suitable functional groups include acid, alcohol and/or sulphone. Linkage after polymerization helps to minimize loss of the expensive energy donor and energy acceptor moieties.

However, the second monomer units (or single monomer units) may contain the proximity based signal generating/modulating moieties. In this case, the discussion above of suitable polymerisable groups and linkages applies.

In a preferred embodiment, the second monomer units are each N-(3-aminopropyl)methacrylamide or a derivative thereof.

In a preferred embodiment, the single monomer units are each a double bond containing, carbohydrate or carbohydrate mimetic moiety containing derivative of lysine. An example is shown below (multistep reaction scheme):

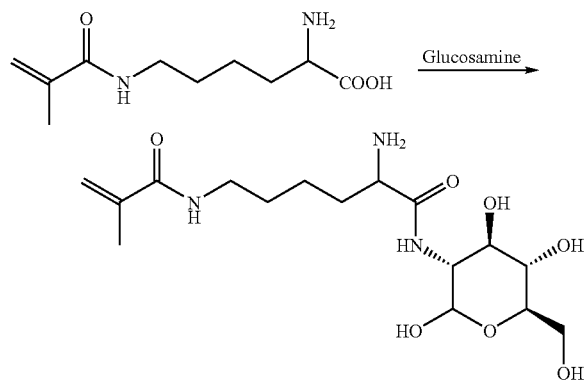

The starting material in this reaction scheme is methacryloyl-L-lysine, available through PolysSciences Europe (Eppelheim, Germany). After polymerization, the alpha amine group could be linked to the proximity based signal generating/modulating moiety.

Preferably, the polymer further contains third monomer unit residues which do not bear pendant carbohydrate or carbohydrate mimetic or proximity based signal generating/modulating moieties. This helps to increase flexibility.

Flexibility is increased by using third monomer units which are sterically unhindered such as HEA. Flexibility is also increased by using third monomer units which are uncharged. A polymer containing no third monomer units would have a large number of positively charged ammonium groups, which would need to be inactivated to minimise decreased flexibility by electrostatic repulsion.

More than one type of third monomer can be included in the polymer.

Preferably, the third monomers units are each a double bond-containing molecule containing a hydrophilic group, for example a hydroxyl group. It is not preferred for the third monomers units to be a lipophilic double bond-containing molecule, for example styrene.

In a preferred embodiment, the third monomer units are each HEA, vinyl pyrrolidone, MMA, HEMA, vinyl alcohol and/or ethylene glycol. However, the skilled person will appreciate that there are many other double bond-containing molecules containing hydrophilic groups which could be used.

Suitably, the monomer units are reacted by addition polymerization. The addition polymerization may be free-radical initiated, for example using potassium peroxodisulfate (PPS) or another peroxide compound.

Other possibilities are condensation polymerization (for example ionic condensation polymerization), ring opening polymerization and atom transfer radical polymerization (ATRP). The skilled person will appreciate that the nature of the monomer units will depend on the desired method of polymerization (for example double bond containing monomer units are not necessary for condensation polymerization).

Suitably, the monomer units are mixed before initiator is added.

Preferably, the polymerization reaction takes less than two days. The length of the polymerization can be used to control the molecular weight of the co-polymer product.

Suitably, the polymerization reaction takes place under oxygen-free conditions.

Suitably, the polymerization reaction is carried out at room temperature.

Where no single monomer units are used, the first monomer units are preferably present in the reaction mixture in an amount of 20 to 70 wt %, more preferably in an amount of 30 to 50 wt %.

Where the third monomer units are used, they are preferably present in the reaction mixture in an amount of 5 to 15 wt %.

It will be appreciated that the composition of the polymer does not exactly reflect the amounts of monomer units present in the reaction mixture. This is because of the influence of other factors (for example steric hindrance and solubility).

In a preferred embodiment, the analyte is glucose, and in each variant of the competitive binding assay the macromolecule and analyte analogue moieties together form a polymer as described above, and the different assay variants are distinguished by number or nature of analyte analogue moieties in the polymer. Preferred polymers include mannose bearing polymers, for example those prepared from allyl-α-D-mannopyranoside as second monomer unit (with different amounts of allyl-α-D-mannopyranoside for the polymers of different variants). Preferably in this embodiment the analyte binding agent is MBL.

It should also be noted that the analyte analogue may consist of two or more separate entities which together act as an analyte analogue. In particular, the analyte analogue may consist of a first entity with at least two analyte analogue moieties and a second entity which is an analyte binding agent such as a lectin. For example, acceptor labelled MBL and donor labelled MBL can be used together with unlabelled dextran or unlabelled synthetic polymer as a template to bring the donor labelled MBL and acceptor labelled MBL in proximity of each other so that FRET occurs. (example using Con A given by Gestwicki et al. (2002) Chemistry and Biology 9, p163).

Preferably, the analyte analogue is labelled as discussed above.

The proximity based signal generating/modulating moieties may be attached to the analyte analogue as discussed in connection with the carbohydrate or carbohydrate mimetic analyte analogue moieties above. For example, labelling of dextran can be achieved by direct divinylsulphone coupling or by amination (as described above) followed by coupling. Where an amine derivatised dextran is used as the analyte analogue, care must be taken to avoid cross linking during attachment of the energy donor or energy acceptor moieties, as this could lead to undesirable precipitation. Methods of derivatising dextran with DVS in order to minimise cross-linking are disclosed in EP594772.

The analyte analogue should have a molecular weight high enough to prevent escape from the sensor but low enough that precipitation does not occur when the analyte analogue binds to the analyte binding agent. Analyte analogues having a weight in the range of 25 to 250 kDa, more preferably 40 to 250 kDa, more preferably still 70 to 150 kDa, highly preferably 100 to 120 kDa, for example 110 kDa are preferred. Analyte analogues based on 110 kDa dextran are particularly preferred.

Optionally, the analyte analogue and analyte binding agent are tethered together.

Sensor Construction

Preferably, the components of the assay are retained by a material which has a pore size that permits diffusion of analyte but not the assay components. However, this selectivity may be achieved in other ways, for example by using a material which allows diffusion of uncharged materials.

Preferably, the different assay variants of the sensor are contained in separate compartments of the sensor. The compartments may be macroscopic or microscopic and preferably are located sufficiently close together to be interrogated by a single measuring device simultaneously. However, the assay variants may be contained in a single compartment, although this is not preferred.

Preferably, the components of the assay are retained by a shell or matrix material. The analyte analogue and/or analyte binding agent may be grafted onto this material. More preferably, the material is biodegradable as described in WO00/02048. Optionally, the sensor may comprise small particles (e.g. a mixture of two or more types of particle or two or more masses of matrix containing the assay variants) retained by a shell of biodegradable material as described in WO03/006992.

In a preferred embodiment, the components of the assay are retained by a shell of biodegradable material encapsulating the assay components whilst allowing glucose to contact the assay components, and the biodegradable material comprises a co-polymer having hydrophobic and hydrophilic units, as described in WO2005/110207.

Preferably, the co-polymer is a random copolymer.

Preferably, the co-polymer has a permeability of at least $5.0 \times 10^{-10}$ cm$^2$/s.

The word "permeability" is used to refer to the overall permeability of analyte (glucose) through hydrated co-polymer which can be measured experimentally.

Preferably, once implanted in the body the co-polymer degrades over a period of one week to one year, for example 30 days. For a typical polymer thickness of 5 μm this corresponds to a degradation rate of 0.17 μm/day.

Preferably, for mobility of glucose, the biodegradable material has a molecular weight cut-off limit of no more than 25000 Da. More preferably, the biodegradable material has a molecular weight cut-off limit of no more than 10000 Da.

Preferably, the weight fraction of the hydrophobic units is from 10 to 90% of the co-polymer, more preferably from 10 to 50% of the co-polymer.

Preferably, the molecular weight of each hydrophilic unit is from 200 to 10000 Da, more preferably from 400 to 4000 Da.

Preferably, the hydrophilic units of the co-polymer each comprise an ester of polyethylene glycol and a diacid. As an alternative to polyethylene glycol, a mixed polymer of ethylene glycol and propylene glycol may be used, and/or the polyether backbone may be substituted with hydrophobic and/or hydrophilic groups. As a further alternative to polyethylene glycol, poly-tetrahydrofuran (poly-THF) may be used.

Preferably, the hydrophilic units comprise terephthalic acid and/or succinic acid as diacids. Other suitable diacids are oxalic acid, tartaric acid, phthalic acid, aspartic acid, malonic acid and oligomeric or polymeric diacids, for example poly (dimer acid-sebacic acid). In one preferred embodiment, the diacid is terephthalic acid only. In an alternative preferred embodiment, the molar ratio of terephthalic acid to succinic acid is 1:2 to 2:1, suitably 1:1.

Alternatively, the hydrophilic units of the co-polymer may comprise oligomers. Suitable oligomers are oligomers of hydroxyethylmethacrylate (HEMA), vinylpyrrolidone, vinyl alcohol, carbohydrates, ethylene oxide and/or 2-acrylamido-2-methyl propane sulfonic acid. Where the hydrophilic units comprise HEMA, biodegradable linkages (for example ester linkages such as terephthalate linkages) are provided within the polymer to increase biodegradability.

Preferably, the molecular weight of each hydrophobic unit is from 400 to 5000 Da.

Preferably, the hydrophobic units of the co-polymer comprise an ester of butane-1,4-diol and a diacid. As an alternative to butane-1,4-diol, pentane-1,5-diol or hexane-1,6-diol may be used.

Preferably, the hydrophobic units comprise terephthalic acid and/or succinic acid as diacids. In a preferred embodiment, the molar ratio of terephthalic acid to succinic acid is 1:2 to 2:1, suitably 1:1.

Alternatively, the hydrophobic units comprise terephthalic acid only as diacid. Other suitable diacids are given above.

Alternatively, the hydrophobic units of the co-polymer can comprise oligomers of methylmethacrylate (MMA), polyurethane and/or amides (for example Nylon-6, oligo-N-tertiary butylacrylamide or oligo-N-isopropylacrylamide). Where the hydrophobic units comprise MMA, biodegradable linkages (for example ester linkages such as terephthalate linkages) are provided within the polymer to increase biodegradability.

Preferred polymers have the general formula aPEG(T/S)bPB(T/S)c where "a" denotes the molecular weight of the PEG chain, "b" the weight fraction of the PEG(T/S) (polyethylene glycol terephthalate/succinylate) in the resulting polymer and "c" the weight fraction of the PB(T/S) (polybutylene terephthalate/succinylate) in the resulting polymer. Examples of such polymers are 600PEGT80PBT20, 1000PEGT80PBT20, 2000PEGT8.0PBT20, 4000PEGT80PBT20, 1000PEGT50PBT50 and 1000PEG(T/S)60PB(T/S)40(T/S 50%). The polymers are biodegradable, have high glucose permeability and have molecular weight cut-off properties at around 25000 Da.

Some of these polymers are disclosed in U.S. Pat. No. 6,383,220 and EP1247522.

The envelope of co-polymer preferably has a thickness of 1 to 50 μm.

In a second aspect, the present invention relates to a method of preparing a sensor as described herein.

Chemical methods for the preparation of polymer microcapsules include phase separation (coacervation), solvent evaporation and/or extraction.

Suitable physical methods for the preparation of polymer microcapsules include spray drying, spray coating, spray chilling, rotary disk atomisation, fluid bed coating, coextrusion (for example stationary nozzle coextrusion, centrifugal head coextrusion, or submerged nozzle coextrusion) and pan coating.

Sensor Use

In a third aspect, the present invention relates to a method of detecting glucose using a sensor as described herein, comprising implantation of the sensor into the skin of a mammal and detection or measurement of glucose using external optical means.

In a fourth aspect, the present invention relates to a method of detecting glucose using a sensor as claimed described above, comprising detection or measurement of glucose using external optical means by illumination of a said sensor present in or below the skin of a mammal.

Preferably, the method further comprises degradation of biodegradable material in the sensor.

The sensor may be introduced within the skin by injection, preferably using a syringe, or by other methods, in particular by any method described in WO00/02048. The sensor is preferably of a size suitable for injection through a narrow gauge needle to minimise the discomfort to the patient. Preferably, the sensor has a maximum dimension of 20 µm to 1 mm. However, a rod-shaped sensor having a larger maximum dimension may be used.

The sensor may be introduced within the thickness of the dermis, or subdermally, or may be introduced to the epidermis, although in the latter case it would be likely to be expelled from the skin by outgrowth of the epidermal layers, possibly before the biodegradable material has degraded.

Because the sensor is located within the skin, an optical signal generated in the sensor is preferably detected transcutaneously (i.e. through the higher layer(s) of the skin) thus obviating the need for any direct connection between the sensor and the external environment which may lead to infection.

However, detection may alternatively take place via a hollow or transparent means (for example a needle or optical fibre) which allows the sensor to be illuminated by external optical means without passing light through the skin.

Once the sensor is in place in a cutaneous location glucose measurements can be taken as often as is necessary with no adverse effects. This is a particular advantage in relation to the long-term care of diabetic patients because if glucose measurements are taken more frequently, tighter control can be maintained over the level of glucose in the blood and the risk of developing conditions related to poorly regulated blood glucose, such as retinopathy, nephropathy, neuropathy, general micro- and macrovascular damage and poor circulation, will be reduced.

Because the sensor of the invention does not itself contain any of the optical components required to interrogate the readout of the assay (these being preferably provided separately and located outside the body) the sensor can easily be provided in a form which is injectable with minimal discomfort to the patient.

Sensors incorporating an assay employing the technique of FRET may be interrogated by supplying incident radiation at a wavelength within the absorption spectrum of the energy donor moiety and measuring the intensity of the emitted fluorescence or the lifetime of the excited state. Commonly known methods are:

1 Steady state measurement
2. Time-domain lifetime measurement
   a. Single photon counting
   b. Streak camera
   c. Gated detection (pulse sampling)
   d. Up-conversion
3. Frequency domain lifetime measurement
   a. Phase-modulation fluorometry (heterodyne detection)
   b. Phase sensitive detection (homodyne detection)

Further description of the principles may be found in Lakowicz, J. R. "Principles of Fluorescence Spectroscopy, Second Edition", 1999.

The preferred method for interrogating the assay is phase-modulation fluorometry.

A suitable optical set-up for interrogating the assay (FIG. 7) consists of a light-emitting diode (LED) 11, which emits light within the emission spectrum of the energy donor moiety. The LED is operated by a driver circuit 13, which modulates the LED at a frequency which results in a sufficient phase shift, preferably in the range of 45°. For a fluorophore with a lifetime of 3 ns, the preferred frequency is 50 MHz. The light emitted by the LED is filtered by an excitation filter 15 and directed towards the sensor 16 by a dichroic beam splitter 17 and focused onto the sensor/skin above the injected sensor 16 by a lens 19. The fluorescence emitted by the sensor is collected by the lens 19. The light passes through the dichroic beam splitter and is filtered through an emission filter 21. The filtered light is focused by a lens 23 onto the detector 25, in this case an avalanche photodiode (APD). The APD is reverse biased by an APD bias supply 27, which is controlled by a signal processing and control unit 29. The signal from the APD is amplified by a trans-impedance amplifier 31, filtered by a bandpass filter 33 and sampled by a first analog-to-digital converter (ADC) 35. Correspondingly, the modulated drive signal to the LED is sampled by a second ADC 37. The signal sampled on the first ADC 35 is:

$$Y_1(t) = A_1 * \sin(2*\pi*f*t + \phi_{f1} + \phi_1)$$

$A_1$ is the amplitude of the detected signal from the assay,
f is the modulation frequency, $\phi_{f1}$ is the phase lag introduced by the donor fluorophore and $\phi_1$ is a fixed phase lag introduced by the electronic and optical set-up.

The signal sampled on the second ADC 37 is:

$$Y2(t) = A_2 * \sin(2*\pi*f*t + \phi_2)$$

$A_2$ is the amplitude of the modulated drive signal to the LED and $\phi_2$ is a fixed phase lag introduced by the electronic set-up The signal processing and control unit derives the phase lag $\phi_{f1}$ introduced by the energy donor moiety by comparing the two sampled signals and compensating for the fixed and known phase lags introduced by the electronics and optics.

Measurements are taken by holding the fluorometer close to the skin and in alignment with the sensor. The phase lag is converted to analyte concentration by the use of a phase-to-analyte-calibration function, such as $$\text{analyte concentration} = A + Bx/(k+x),$$

where A is the phase at no analyte present, B is the phase at maximal response, x is the measured phase, and k is the dissociation constant between the receptor and the analyte analogue.

An alternative measurement technique is measurement of fluorescence intensity.

In this case, the optical means should supply a first beam of incident radiation at a wavelength within the absorption spectrum of the energy donor moiety and preferably a second beam of incident radiation at a wavelength within the absorption spectrum of the energy acceptor moiety (this applies where the energy acceptor moiety is also a fluorophore). In addition, the optical means should preferably be capable of measuring optical signals generated in the sensor at two different wavelengths; wavelength 1 within the emission spectrum of the energy donor moiety (the signal generated in connection with the measurement of analyte) and wavelength 2 in the emission spectrum of the energy acceptor moiety (which could be the analyte signal or the internal reference or calibration signal).

The fluorimeter separately measures the following parameters:

At wavelength 1 (energy donor moiety)
Excitation light intensity, I(1,0)
Ambient light intensity, I(1,1)
Intensity of combined fluorescent and ambient light, I(1,2)
At wavelength 2 (energy acceptor moiety)
Excitation light intensity, I(2,0)
Ambient light intensity, I(2,1)
Intensity of combined fluorescent and ambient light, I(2,2)

Again, measurements are taken by holding the fluorimeter close to the skin and in alignment with the sensor. When making transcutaneous measurements of the fluorescent signals generated in the sensor it is necessary to take account of the absorption of signal by the skin. The absorptivity of human skin is found by experiment to be lowest in the range from 400 nm to 900 nm. The final output provided is the normalised ratio between the fluorescent intensity from the two fluorophores, defined by the following relation (Equation 1):

$$\text{Final output} = (I(1,2) - I(1,1)) * I(2,0) / (I(2,2) - I(2,1)) * I(1,0) \quad (1)$$

The final output from the optical means (e.g. the fluorimeter) as given by Equation 1 above is converted to analyte concentration preferably by means of a computer using calibration data which can be obtained based on the principles set out in WO00/02048.

The invention will be further illustrated with reference to examples, and to the Figures in which.

EXAMPLES

General

Figure 1:
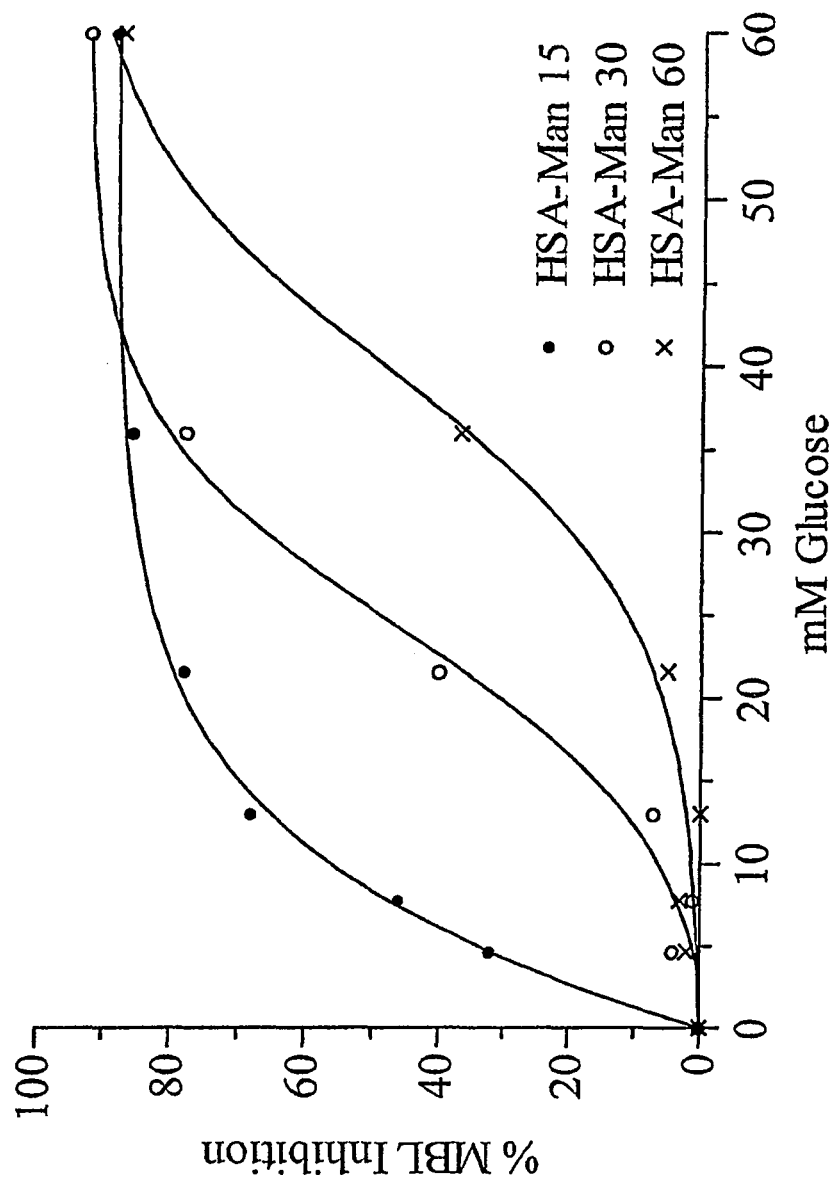
FIG. 1 shows the glucose dose response from a human MBL and HSA mannose ELLA assay system (Example 1)

The following materials were used:
p-Aminophenyl-α-D-mannopyranosyl isothiocyanate, bovine serum albumin-α-D-mannopyranosyl isothiocyanate (23 molar equivalents mannose per BSA), human serum albumin, sodium periodate ($NaIO_4$), biotin-N-hydroxysuccinimide, o-phenylene dihydrochloride, benzylamine, ammonia, sodium cyanoborohydride ($NaBH_3CN$) (Sigma-Aldrich); Nunc F96 MaxiSorp plate (Nunc, Denmark); PD-10 columns, Streptavidin-HRP (Amersham Bioscience); dextrans (Pharmacosmos, Denmark); mannan binding lectin (available from several sources); dialysis tube Spectra/Por (Spectrum Laboratories, Inc., California, USA). Allyl α-D-Glucopyranoside, Allyl 2-acetamido-2-deoxy-α-D-glucopyranoside (Glycon Biochemicals, Germany). Allyl α-D-Galactopyranoside (Sigma-Aldrich).

PBS is 20 mM Phosphate, 150 mM NaCl, pH 7.4, and TBS is 20 mM TRIS, 150 mM NaCl, 1.25 mM $CaCl_2$, pH 7.4 unless otherwise stated.

Abbreviations: MBL, Mannan Binding Lectin; PBS, Phosphate buffered saline; TBS, TRIS buffered saline; ELLA, Enzyme Linked Lectin Assay.

Preparation of Biotinylated MBL

Biotin-NHS (20 µL, 7 $mgmL^{-1}$ in DMSO, ca. 10-15 molar equivalents per MBL monomer) was added to a solution of MBL (0.530 mg) in PBS (3 mL). The solution was gently stirred for 2 h, and then transferred to a dialysis tube (MWCO 10-12k) and dialysed against TBS (2×1 L) over the course of 24 h. The resulting biotinylated MBL (0.2 $mgmL^{-1}$ in TBS) was used without further purification.

MBL ELLA Assay

The TBS buffer used herein was TRIS (20 mM), NaCl (150 mM), $CaCl_2$ (20 mM), pH 7.4.

A 96-well microtitre plate was coated overnight at 5° C. with two columns of each of the antigens (e.g., HSA-mannose, aminodextran, etc) (100 µL, 20 $µgmL^{-1}$) in TBS.

Residual binding sites were then blocked by the addition of 1% (w/v) HSA in TBS (150 µL). Dilutions of glucose (from 100 mM to 0 mM) in biotinylated MBL (2 $µgmL^{-1}$) were added to a total volume of 100 µL. After incubation for 2 h, the plate was emptied and washed (2×200 µL TBS). The wells were then washed (2×200 µL TBS). Streptavidin-HRP 0.1% (v/v) (100 µL) in TBS was added. Following 1 h incubation, plates were emptied and washed (3×200 µLTBS). The presence of HRP was visualised by the addition of substrate solution (1 mg o-phenylene dihydrochloride) and quenched after 2 min with 1 N $H_2SO_4$. Colour development was determined by reading the absorbance at 490 nm, with background subtraction at 630 nm.

Example 1

Mannosylated HSA

Four conjugates were prepared in the following way. To each of four 2 mL Eppendorf vials were added HSA (10 mg) dissolved in a 20 mM carbonate buffer (0.4 mL, pH 9.2).

p-Aminophenyl-α-D-mannopyranosyl isothiocyanate (Man-ITC, 1.6 mL) were added in 15×, 30×, 60× and 120× molar excess by preparing four solutions.

Man-ITC (11.9 mg) was dissolved in DMSO (0.1 mL) and 20 mM carbonate buffer pH 9.2 (3.9 mL). An aliquot (1.6 mL) of this solution (corresponding to 120× molar excess) was added to an Eppendorf vial containing HSA (0.4 mL). The rest of the Man-ITC solution was diluted to double volume, and from the diluted volume an aliquot (1.6 mL) was added to another Eppendorf vial. This procedure was repeated until the four different HSA:Man-ITC mixtures had been prepared. The four reaction mixtures were incubated in a shaker overnight at room temperature.

The resulting glycoconjugates were purified on a PD-10 column. During the purification, the buffer was changed to TBS.

The degree of conjugation was determined using MALDI-TOF-MS.

|  | m/z (MALDI-TOF) | Number of mannose per HSA |
|---|---|---|
| HSA-Mannose 1:15 | 67500-70000 | 3-11 |
| HSA-Mannose 1:30 | 67700-70600 | 4-13 |
| HSA-Mannose 1:60 | 68100-72300 | 5-18 |
| HSA-Mannose 1:120 | 68600-73400 | 7-22 |

Table 1: Determination of conjugation degree using MALDI-TOF-MS. Peak width estimate was measured around half height. The number of mannose units was determined using the following formula: (Peak in MS-66500)/313.

When used in the competitive binding assay, the different glycoconjugates were found to have different avidities for MBL, and therefore were competitively binding in the presence of different ranges of concentration of glucose. The MBL ELLA assay described above was used to determine the effect of the degree of mannosylation on the dynamic range for glucose inhibition, and the results are shown in FIG. 1.

The glucose concentration range over which the dosage response curve is linear for a particular glycoconjugate in FIG. 1 corresponds to the glucose concentration range over which the competitive binding assay variant containing that glycoconjugate may accurately detect glucose. It may be seen from FIG. 1 that the use of the three glycoconjugates HSA-Man 15, HSA-Man 30 and HSA-Man 60 in three competition assay variants within the sensor of the present invention may permit the accurate measurement of glucose concentration over the range 0-50 mM glucose.

Example 2

Periodate Oxidised Dextran for use in ELLA Assay

Preparation of Periodate-Oxidised Dextran

Dextran 70k (200 mg, 2.86 mmol) was dissolved in water (2.8 mL) and added to $NaIO_4$ (100 mM, 10× molar excess) in water (2.8 mL). The mixture was stirred in the dark for 1 h at room temperature. The resulting mixture was transferred to a dialysis tube (MWCO 10-12k) and dialysed overnight against 5 L water.

After dialysis, the volume was adjusted to 8 mL. The periodate-oxidised dextran was split into two aliquots (4 mL, 100 mg each) and treated for 30 min with 28% aqueous ammonia (200 μL) and benzylamine (300 μL), respectively. The imine and iminium derivatives were then reduced with $NaBH_3CN$ (45 mg) overnight at room temperature and pH around 10.

The reaction mixture was dialysed against 2×1 L 20 mM TRIS the following day.

The degree of amine incorporation into the periodate-oxidised dextran was determined using elemental analysis.

MBL ELLA Assay

The assay described above was used, except with a TRIS buffer containing 1.25 mM $CaCl_2$ (physiological Ca concentration).

Figure 2:
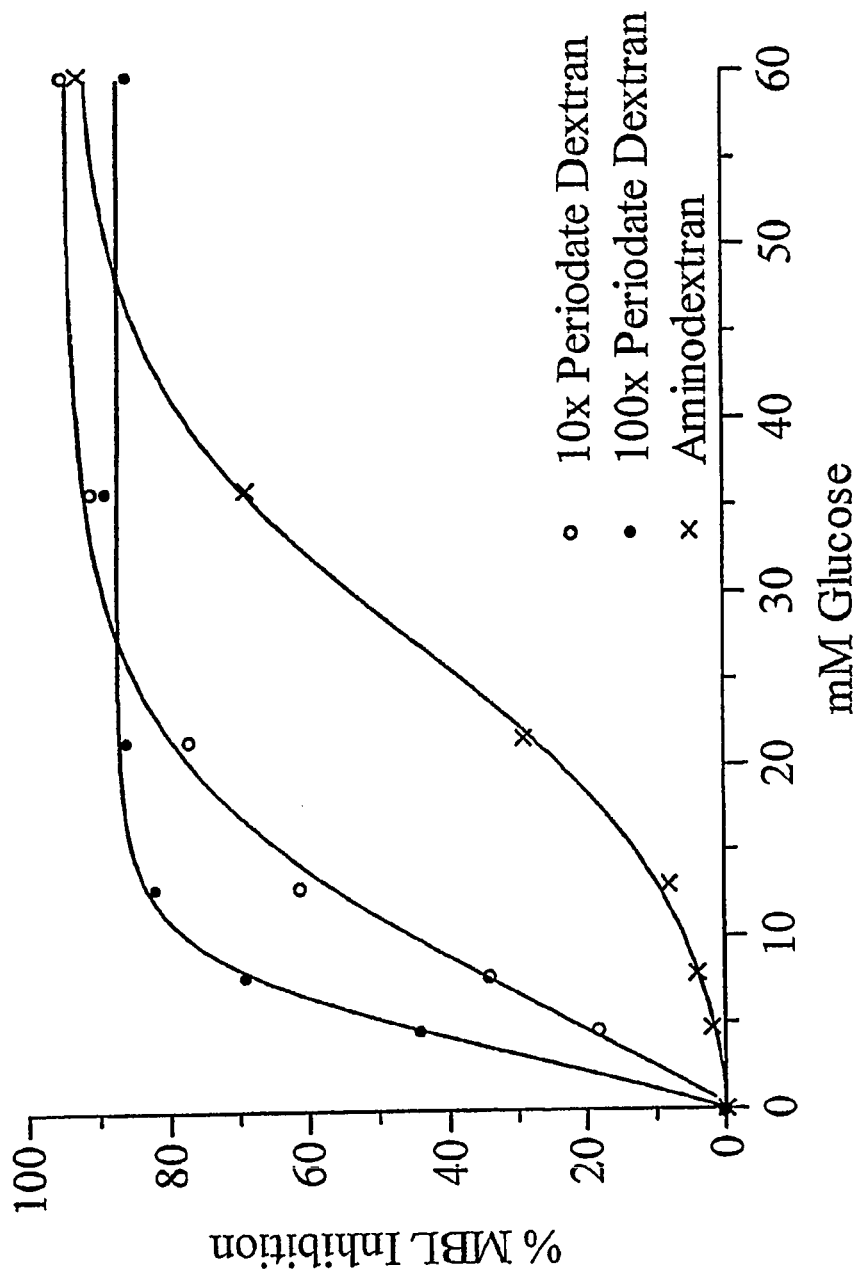
FIG. 2 shows the glucose dose response from a human MBL and periodate treated dextran ELLA assay system (Example 2).

The results of the ELLA assay comparing aminodextran, dextran oxidised in the presence of 10× molar excess of periodate and reductively aminated using benzylamine, and dextran oxidised in the presence of 100× molar excess of periodate and reductively aminated using benzylamine are shown in FIG. 2.

It can be seen from inspection of FIG. 2 that the range over which glucose concentration may be accurately measured may be 0-35 mM glucose when using three competitive binding assays in combination, each containing one of the three aminodextrans. The binding of the aminodextrans to MBL is found to be essentially $Ca^{2+}$-independent, and so these assays may be used at physiological $Ca^{2+}$ concentrations.

Example 3

Synthetic Polymer for use in ELLA Assay

Allyl α-D-Mannopyranoside

Essentially as described in Pekari et al. (2004) *J. Org. Chem*, 66(22), 7432-7442. D-Mannose (12.1 g, 67 mmol) was refluxed overnight in dry allyl alcohol (140 ml) in the presence of $BF_3$—$OEt_2$ (0.58 ml). The reaction mixture was neutralised with $Et_3N$ (1.8 ml) the following day, and the solvent evaporated. Dry Column Vacuum Chromatography (id 6 cm; 100 ml fractions; 0-45% MeOH in DCM (v/v)–11 fractions, 5% increments+100%) afforded the product 9.38 g (63%) as a colourless syrup. TLC (DCM-MeOH, 9:1) $R_f$ 0.3;

$^1$H-NMR (300 MHz, 128 scans, 4 mg in 700 μl $D_2O$) δ 3.27 (s, 2H, Allyl), 3.52-4.21 (m, 6H), 4.84 (bs, 1H, αH), 5.16-5.34 (m, 2H, Allyl), 5.82-5.98 (m, 1H, Allyl).

Copolymerization

The following example illustrates how the Mannose 50% copolymer is prepared. See Tables 2 and 3 for all other copolymer preparations. Stock solutions (100 mg/ml) of Allyl-saccharides (AS) and N-(3-aminopropyl)methacrylamide hydrochloride (NAMH) were prepared in PBS (50 mM, pH 7.4).

Potassium peroxodisulfate (PPS) (150 mg) was dissolved in PBS buffer (50 mM, pH 7.4; 7.8 ml) in a screw-capped plastic tube. To this solution was added in the following order Allyl α-D-Mannopyranoside (Allylsaccharide; AS)(2.20 ml; 220 mg), 2-hydroxyethylacrylate (HEA)(110 μl), N-(3-aminopropyl)methacrylamide hydrochloride (NAMH)(89 ρl) and N,N,N',N'-tetramethylethylenediamine (TMEDA)(100 μl). The mixture was purged with nitrogen for 5 min to remove dissolved oxygen. Polymerization was carried overnight at RT in an orbital shaker. The reaction mixture was filtered and precipitated in methanol (100 ml). The polymer was collected by centrifugation (4000 rpm, 3 min) and then washed with methanol (3×10 ml). The final obtained polymer pellet was dried overnight in an exiccator.

TABLE 2

| Calcd. saccharide molar fraction | AS (ml) | HEA (μl) | NAMH (μl) | PBS (ml) | PPS (mg) | TMEDA (μl) | Polymer yield (mg) |
|---|---|---|---|---|---|---|---|
| Mannose 10% | 0.44 | 203 | 89 | 9.56 | 150 | 100 | 95 |
| Mannose 30% | 1.32 | 157 | 89 | 8.68 | 150 | 100 | 119 |
| Mannose 50% | 2.20 | 110 | 89 | 7.80 | 150 | 100 | 164 |
| Mannose 70% | 3.08 | 64 | 89 | 6.92 | 150 | 100 | 171 |
| Mannose 90% | 3.96 | 17 | 89 | 6.04 | 150 | 100 | 152 |
| GlcNAc 10% | 0.75 | 203 | 89 | 9.56 | 150 | 100 | 114 |
| GlcNAc 30% | 2.26 | 157 | 89 | 8.68 | 150 | 100 | 122 |
| GlcNAc 50% | 3.77 | 110 | 89 | 7.80 | 150 | 100 | 149 |
| GlcNAc 70% | 5.28 | 64 | 89 | 6.92 | 150 | 100 | 159 |
| GlcNAc 90% | 6.80 | 17 | 89 | 6.04 | 150 | 100 | 160 |
| Glucose 10% | 0.44 | 203 | 89 | 9.56 | 150 | 100 | 98 |
| Glucose 30% | 1.32 | 157 | 89 | 8.68 | 150 | 100 | 105 |
| Glucose 50% | 2.20 | 110 | 89 | 7.80 | 150 | 100 | 158 |
| Glucose 70% | 3.08 | 64 | 89 | 6.92 | 150 | 100 | 160 |
| Glucose 90% | 3.96 | 17 | 89 | 6.04 | 150 | 100 | 162 |
| Galactose 10% | 0.44 | 203 | 89 | 9.56 | 150 | 100 | 95 |
| Galactose 30% | 1.32 | 157 | 89 | 8.68 | 150 | 100 | 119 |
| Galactose 50% | 2.20 | 110 | 89 | 7.80 | 150 | 100 | 164 |
| Galactose 70% | 3.08 | 64 | 89 | 6.92 | 150 | 100 | 171 |
| Galactose 90% | 3.96 | 17 | 89 | 6.04 | 150 | 100 | 152 |

TABLE 3

The four different monosaccharides used for copolymerisation

| Allyl-α-D-Mannose | Allyl-α-D-N-Acetyl-glucosamine |
|---|---|
| 10% | 10% |
| 30% | 30% |

TABLE 3-continued

The four different monosaccharides used for copolymerisation

| 50% | 50% |
| 70% | 70% |
| 90% | 90% |
| Allyl-α-D-Glucose | Allyl-α-D-Galactose |
| 10% | 10% |
| 30% | 30% |
| 50% | 50% |
| 70% | 70% |
| 90% | 90% |

MBL ELLA Assay

The assay described above was used, except with a TRIS buffer containing 1.25 mM $CaCl_2$ (physiological Ca concentration).

Figure 3:
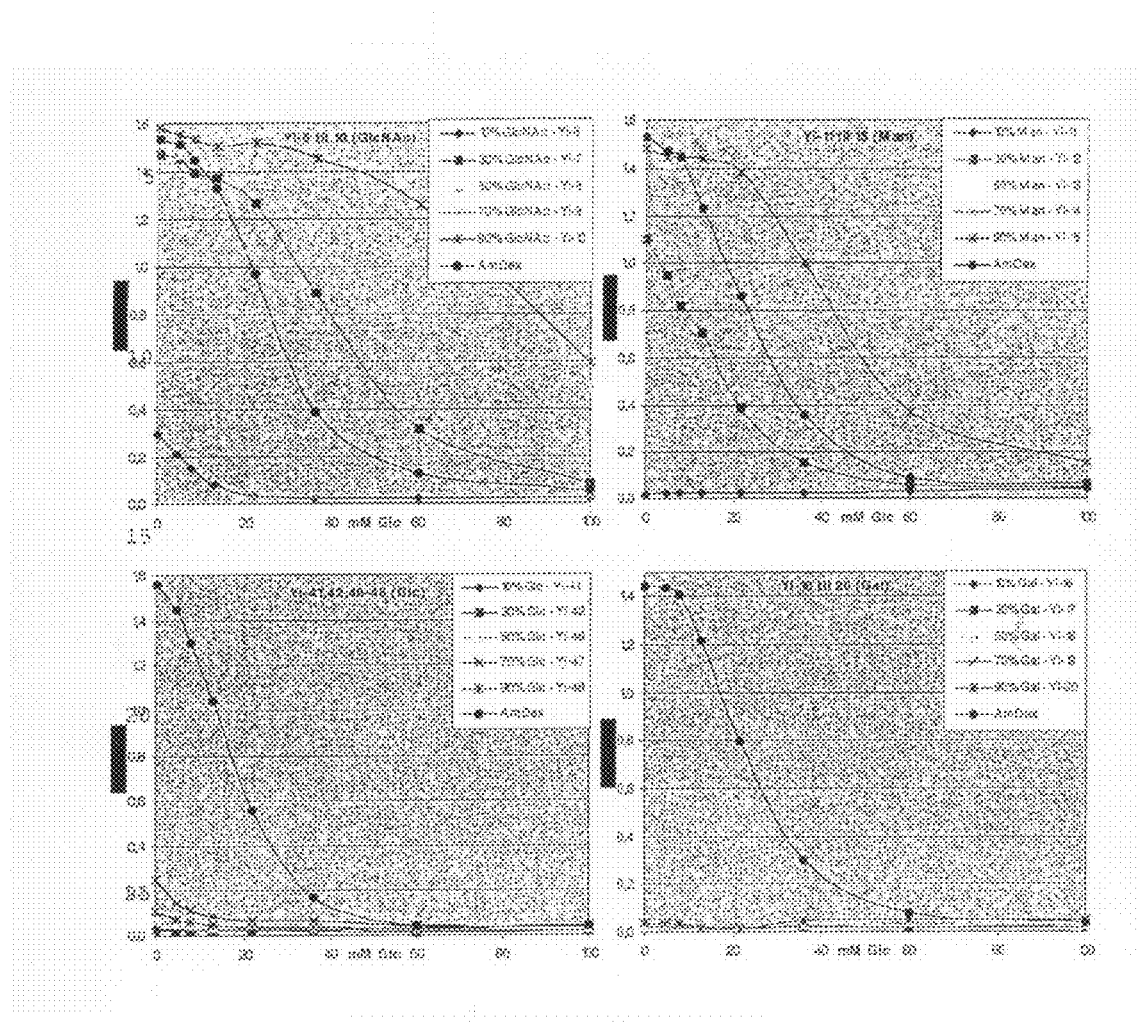
FIG. 3 shows the glucose dose response from a human MBL and synthetic polymer ELLA assay system (Example 3).

The results are shown in FIG. 3, which compares 20 copolymers made out of mannose, N-Acetyl-glucosamine, glucose and galactose. High absorptions correspond to binding of MBL to the ligand. Baseline absorption corresponds to no binding of MBL to the ligand. AmDex is 150 kDa Aminodextran (Example 5).

This demonstrates that the monomeric saccharide unit used in the synthetic polymer needs to have higher affinity to MBL than glucose ($IC_{50}$ ~18 mM), and is preferably mannose ($IC_{50}$ ~8 mM) or N-acetyl-glucosamine($IC_{50}$ ~6 mM). Lower affinity saccharide monomer units, such as galactose ($IC_{50}$ ~36 mM), do not give MBL binding at physiological calcium concentrations (1.25 mM).

Figure 4:
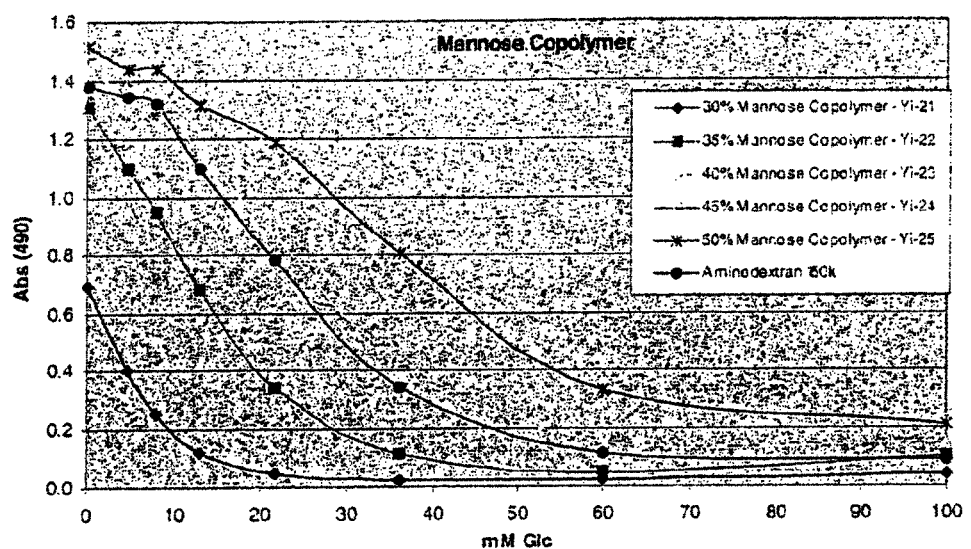
FIG. 4 shows the glucose dose response from a human MBL and synthetic mannose copolymer ELLA assay system (Example 3).

A series of Mannose Copolymers were prepared (Table 4) and assayed using the MBL ELLA assay. It was found that 35% mannose copolymer was optimal. The binding was as strong to MBL at 0 mM glucose, but more easily inhibited than aminodextran. From the inhibition curves (FIG. 4), it is possible to calculate an $IC_{50}$ value for aminodextran and the optimized copolymer (Table 5). The $IC_{50}$ value is only valid for this particular assay.

TABLE 4

| Calcd. saccharide molar fraction | AS (ml) | HEA (µl) | NAMH (µl) | PBS (ml) | PPS (mg) | TMEDA (µl) | Polymer yield (mg) |
| --- | --- | --- | --- | --- | --- | --- | --- |
| Mannose 30% | 1.32 | 157 | 89 | 8.68 | 150 | 100 | 111 |
| Mannose 35% | 1.54 | 145 | 89 | 8.46 | 150 | 100 | 148 |
| Mannose 40% | 1.76 | 134 | 89 | 8.24 | 150 | 100 | 151 |
| Mannose 45% | 1.98 | 122 | 89 | 8.02 | 150 | 100 | 149 |
| Mannose 50% | 2.20 | 110 | 89 | 7.80 | 150 | 100 | 158 |

TABLE 5

| $IC_{50}$ | Glucose (mM) |
| --- | --- |
| Aminodextran | 23 |
| 35% Man Copolymer | 13 |

Example 4

Staining of MBL

Human MBL was buffer changed (by dialysis) to a 10 mM $NaHCO_3$ buffer containing 150 mM NaCl and 1.25 mM $Ca^{2+}$, pH 8.7. The dye used for staining was Alexa Fluor™ 594 succimidyl ester (AF594-SE) (Molecular Probes, Eugene, Oreg., USA). The dye was dissolved in dry DMSO and added slowly (10 min.) to the MBL in bicarbonate buffer. Reaction was allowed to take place for 1 hour. The staining was performed with 15 times molar excess (with respect to the polypeptide unit) of dye. Purification was carried out by dialysis against 10 mM Tris buffer pH 7.4, 150 mM NaCl and 1.25 mM $Ca^{2+}$. The obtained degree of labelling of the stained protein was determined by UV spectroscopy as 2.3 dyes per subunit of MBL.

Example 5

Preparation of Aminodextran 150 kDa Dextran (6.00 g, 0.4 µmol) was dissolved in 250 mM $K_2HPO_4$ pH 11.5 (600 mL). Sodium borohydride (3 g, 0.08 mol) was added followed by the addition of divinylsulfone (15 ml, 0.15 mol). The reaction mixture was stirred for 30 min at RT, before neutralization to pH 7.2 with conc. HCl.

After 30 min stirring, the resulting mixture was dialysed (MWCO 10-12 kDa) in water (3×25 L). The contents were transferred to an Erlenmeyer flask and 24% ammonia (200 mL) was added. After 2 h, the pH was adjusted to 10.5, and the reaction was stirred overnight. Excess ammonia was removed by dialysis (MWCO 10-12k) in water (8×25 L), and the entire contents were lyophilised to yield the aminodextran 5.75 g (78%, based on an aminodextran MW of 185 kDa) as a white fluffy substance. Elemental analysis was used to make a rough estimate of the molecular weight, amine incorporation, and amount of incorporated divinylsulfone. (Found C, 39.86; H, 6.26; N, 0.16; S 3.08% Dextran 150k, ~22 DVS—$NH_2$, ~160 DVS—OH, and ~720 $H_2O$ requires C, 39.55; H, 6.60; N, 0.16; S 3.07%)

Example 6

Preparation of Hexa-methoxy-crystal Violet succimidyl ester (HMCV-1)

Synthesis of HMCV-1

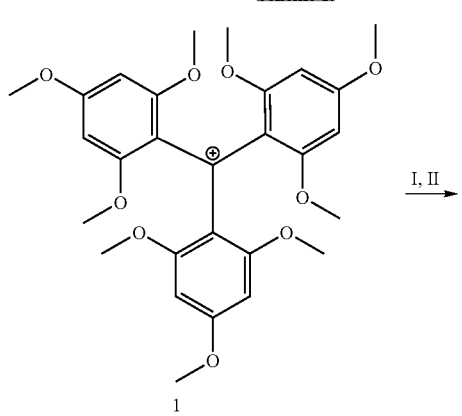

Scheme 1.

I, II

1

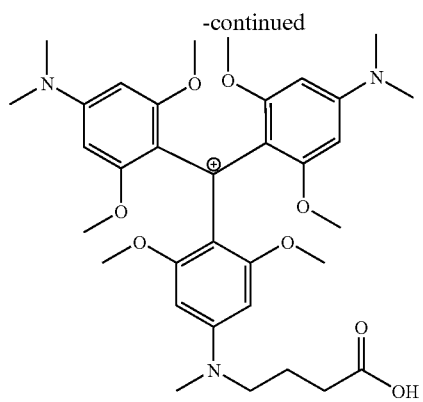

C$_{34}$H$_{46}$N$_3$O$_5^+$
Exact Mass: 624.33
Mol. Wt. (BF4-): 711
4a

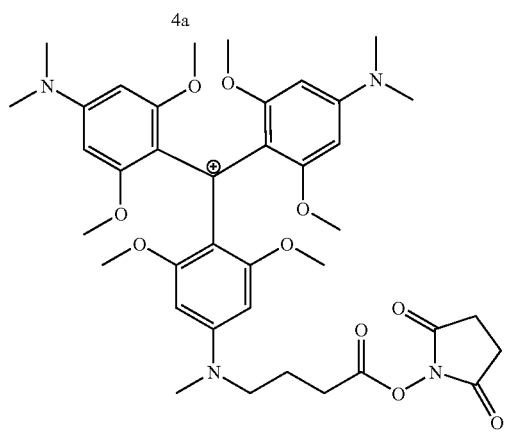

C$_{38}$H$_{49}$N$_4$O$_{10}^+$
Exact Mass: 721.34
Mol. Wt. (Cl-): 757
HMCV-1

I) 4-(N-methylamino)-butanic acid hydrochloride (1 eq.), Diisopropylethylamine, in acetonitrile, 20° C., 20 hours.
II) Dimethylamine (excess).
III) TSTU, Diisopropylethylamine, in acetonitrile, 20° C., 2 hours.

4a (BF$_4^-$): 4-(methylamino)butyric acid hydrochloride (1.36 g; 8.8 mmol), 1 (5.0 g; 8.3 mmol), and diisopropylethylamine (5 mL) was dissolved in acetonitrile (120 mL). The reaction mixture was stirred at 30-35° C. in a dry nitrogen atmosphere for 22 h. Aqueous dimethylamine (40 mL of a 40% solution) was added and the reaction mixture was stirred for four more days. Solvent and excess dimethylamine were removed in vacuo and the remaining material dissolved in chloroform. The chloroform solution was washed twice with brine and dried over MgSO$_4$ before evaporation of the solvent and reprecipitation of the product from CH$_2$Cl$_2$/ether. Yield: 4.4 g (70%) of a dark blue powder.

MS (FAB+): m/z 624 (M+)
$^1$H-NMR (400 MHz, DMSO-d$_6$): δ 8.34 (1H, bs), 6.03 (2H, s), 5.83 (4H, s), 3.49 (2H, m), 3.46 (6H, s), 3.44 (12H, s), 3.12 (3H, s (masked)), 3.08 (12H, s), 1.94 (2H, t), 1.70 (2H, m).

HMCV-1 (Cl$^-$): TSTU (2-succinimido-1,1,3,3-tetramethyluronium tetrafluoroborate; 0.8 g, 2.6 mmol) was added to a solution of 4a (0.9 g, 1.26 mmol) and diisopropylethylamine (0.55 g, 4.5 mmol) in acetonitrile (15 mL). The reaction mixture was stirred in a closed flask for 2 h, before it was poured into an ice-cold nearly sat. NaCl solution (approx. 150 mL) acidified with HCl-aq (4 mL, 2 M). The water phase was extracted with chloroform (2×150 mL). The combined chloroform phases was washed with brine (2×50 mL) and dried over MgSO$_4$.

Evaporation of the solvent and reprecipitation from CH$_2$Cl$_2$/ether gave a dark blue powder (0.80 g, 84%).

MS (FAB+): m/z 721 (M+)
$^1$H-NMR $^1$H-NMR br. (400 MHz, DMSO-d$_6$): δ 5.88 (2H, s), 5.85 (4H,s), 3.60 (2H, s), 3.46 (12H, s), 3.45 (6H, s), 3.15 (12H, s), 3.12 (3H, s), 2.85 (4H, s), 2.80 (2H, t), 1.95 (2H, m).

Example 7

Staining of Aminodextran 70 kDa aminodextran (0.5 mmol NH$_2$/g dextran, i.e. 35 moles amine per mole dextran) prepared by an analogous method to that of Example 2 was stained in 10 mM NaHCO$_3$ pH 8.5, 150 mM NaCl with HMCV-1 (Example 5). The dye was dissolved in dry DMSO and added slowly (10 min.) to the dextran in bicarbonate buffer. Reaction was allowed to take place for 1 hour. The staining was performed with 8 times molar excess of dye. Purification was carried out by dialysis against 10 mM Tris buffer pH 7.4, 150 mM NaCl, 1.25 mM Ca$^{2+}$, 2 mM NaN$_3$. The obtained degree of labelling of the stained protein was determined by UV spectroscopy as 7.0 dyes per dextran.

Example 8

Glucose Measurement for HMCV-1 Dextran

AF594 stained human MBL (Example 1) and HMCV1-Dextran (prepared as in Example 7) were mixed in TBS buffer (same as above) to concentrations of 10 μM of both components. The assay chemistry mixture was sucked into a hollow fibre (regenerated cellulose, diameter 0.2 mm). Fluorescence lifetime measurements (frequency domain) were performed in a KOALA automated sample compartment (ISS, Champaign Ill.) and the glucose concentration was changed by changing the buffer (TBS) around the hollow fibre containing the assay chemistry.

TABLE 6

Absolute phase shifts for AF594-MBL and HMCV1-Dex70. The PMT counts reflect the intensity increase of the system.

| Glu (mM) | Phase @61 MHz 10 μM/10 μM | PMT counts 10 μM/10 μM |
|---|---|---|
| 0 | 36.1 | 3230 |
| 2.5 | 36.6 | 3370 |
| 5 | 37.4 | 3590 |
| 10 | 38.0 | 4030 |
| 25 | 39.2 | 4950 |
| 50 | 40.2 | 5770 |
| 500 | 41.7 | 7220 |

Example 9

Glucose Measurement for Synthetic Polymer

Co-polymer Synthesis
Mannose copolymers (~40%) were prepared by emulsion polymerisation as follows.

To a 250 ml three-necked round-bottomed flask equipped with a mechanical stirrer and a nitrogen tube was added Span80 surfactant (5.7 g; HLB [hydrophile lipophile balance] 4.3, 10% w/w based on toluene), AIBN (30 mg) and toluene (57.3 g). The flask was sealed, purged with nitrogen, and kept under a nitrogen atmosphere throughout the polymerisation. Allyl α-D-Mannopyranoside (3.52 g), 2-hydroxyethylacrylate (2.552 g), and N-(3-aminopropyl)methacrylamide hydrochloride (0.178 g) were dissolved in water (12.7 g) and filtered to remove insoluble material. This mixture was added to the vigorously stirred mixture in the round-bottomed flask through a rubber septum. The reaction mixture was stirred at room temperature until a stable emulsion was formed (30 min), then at 60° C. for 4 h. A solution of VA-044 (1 ml, 60 mg/ml) was injected through the septum and polymerisation was continued overnight (17 h). The reaction mixture was cooled to room temperature and the emulsion was disrupted by the addition of acetone. This caused precipitation of the polymer, which was collected, redissolved in water, and precipitated by addition of acetone. The product was dried overnight under vacuum to yield 3.2 g (50%) crude light yellow polymer. Part of the crude polymer (1.0 g) was dissolved in water (10 ml), and dialysed (MWCO [molecular weight cut off] 25,000) in water to remove low molecular weight material. Freeze-drying yielded 0.46 g (46%) fluffy white polymer.

45% Mannose copolymer was prepared analogously.

Staining of Co-Polymer

In general the labelling of the co-polymer follows the description provided by Molecular Probes (product information MP00143, Rev. June 2001).

The co-polymer (88.6 mg) was dissolved in 10 mM NaHCO$_3$ solution (3 ml; pH 8.5). The polymer solution was divided equally into three Eppendorf vials. HMCV-1 (Example 3) (19.6 mg; 26.1 μmol) was dissolved in dry DMSO (600 μl). The dye was added to the polymer solutions in 10 μl aliquots every 30 seconds, in such a manner that the first vial in total received 100 μl, the second vial received 200 μl and the third vial received 300 μl. After the addition of the last aliquot, the vials were gently stirred for one hour before the solutions were dialysed (MWCO 10-12,000) in 10 mM TRIS buffer with several buffer changes and until no colour was visible in the dialysis buffer (usually 6-8 buffer changes of 500 ml and 72 hours).

FRET Assay

AF594 stained human MBL (Example 4) and HMCV1-Copolymer were mixed in TBS buffer (same as above) to concentrations of 10 μM of both components (using concentration of MBL-AF594 carbohydrate recognition domains, CRD, each with an Mw of approx 25 kDa). The assay chemistry mixture was sucked into a hollow fibre (regenerated cellulose, diameter 0.2 mm).

Fluorescence lifetime measurements (frequency domain) were performed in a KOALA automated sample compartment (ISS, Champaign Ill.). All solutions were pre-heated to 34° C. in a water bath, and all measurements in the KOALA instrument were recorded at 34° C. The fluorescence cell containing the fibre and fibre-holder assembly was placed in the sample holder of the KOALA, and the fluorescence cell was filled with buffer containing glucose.

The measured phase was an average of at least forty phase-angle recordings. After the completion of a measurement, the fluorescence cell was emptied using a pipette, and refilled with buffer containing the next concentration of glucose. A delay of 20 minutes between measurements was introduced to allow the assay chemistry to reach equilibrium.

To generate a glucose dose-response curve, the phase was measured at 0, 5, 10, 30, 100 and 500 mM glucose. After determination of the phase-angle at 500 mM glucose the fibre was washed several times with 10 mM TRIS buffer over a time period of 60 minutes. At this point the same phase-angle was obtained as for 0 mM Glucose. This demonstrates the reversibility of the assay.

Figure 5:
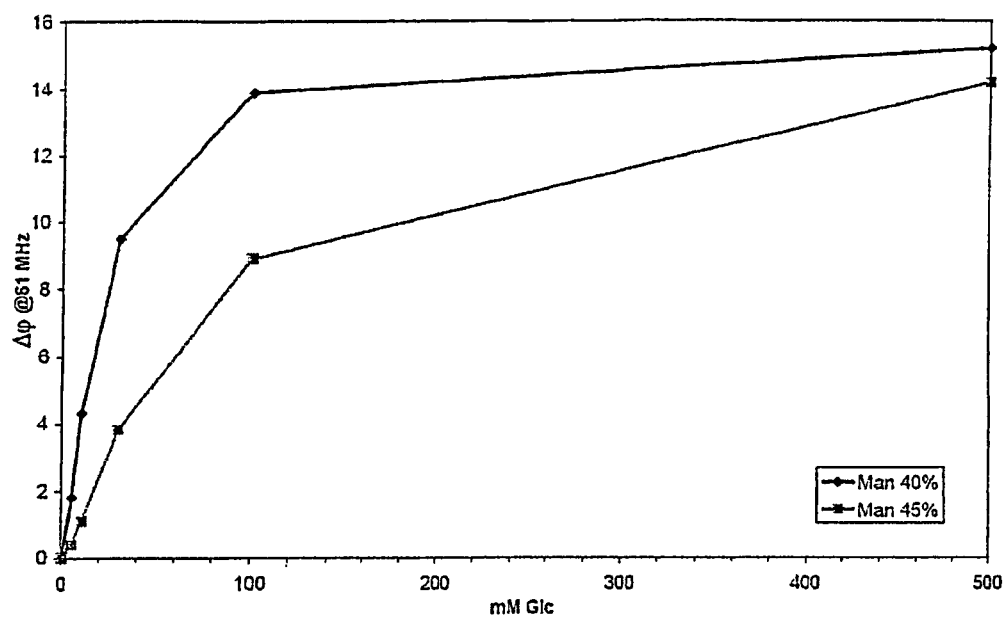
FIG. 5 shows the glucose dose response from a human MBL and synthetic polymer FRET assay system (Example 9).
Figure 6:
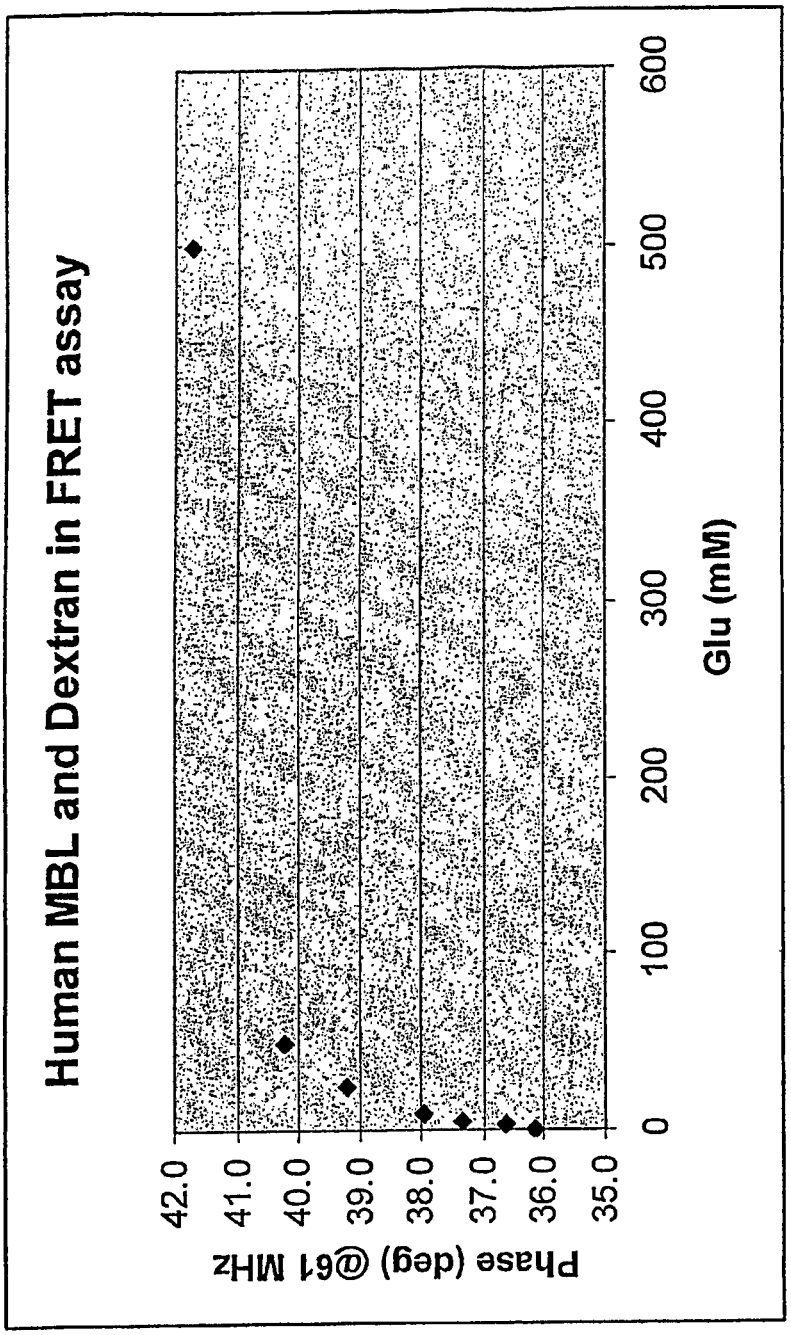
FIG. 6 shows the glucose dose response from a human MBL and 70 kDa dextran FRET assay system (Example 10)
Figure 7:
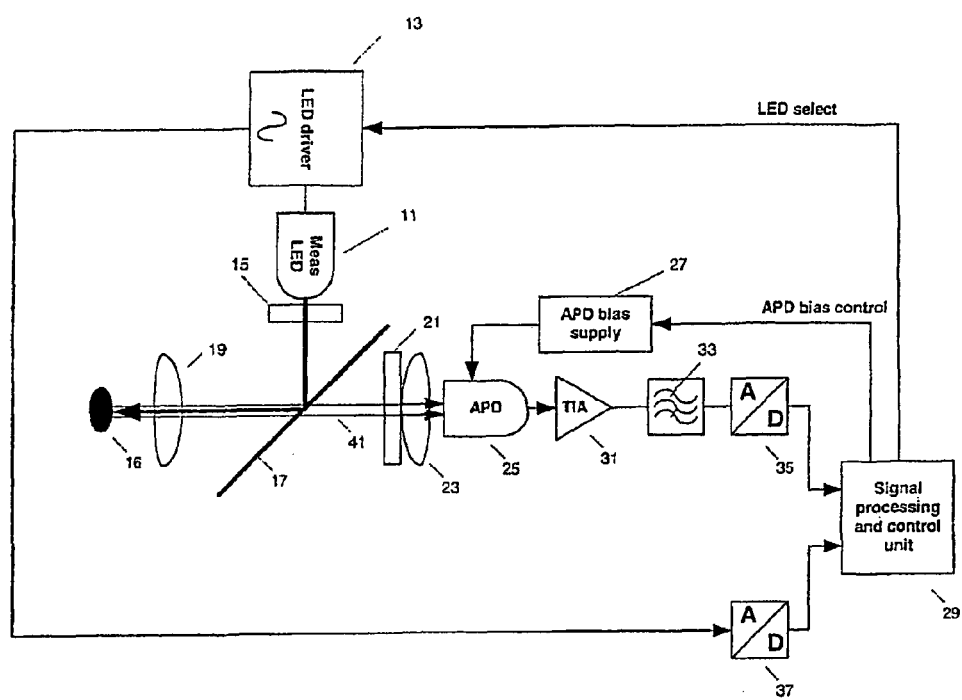
FIG. 7 shows a suitable optical set-up for interrogating the assay.

The results are shown in Table 7 and FIG. 5.

TABLE 7

Absolute phase shifts for AF594-MBL and HMCV1-copolymer.

| mM Glc | □□ @ 61 MHz Mannose 40% copolymer | □□ @ 61 MHz Mannose 45% copolymer |
|---|---|---|
| 0 | 0.0 | 0.0 |
| 5 | 1.8 | 0.4 |
| 10 | 4.3 | 1.1 |
| 30 | 9.5 | 3.8 |
| 100 | 13.9 | 8.9 |
| 500 | 15.2 | 14.2 |

It can be seen that the slope for the mannose 40% copolymer is steeper (more response) in the area 0-5 mM, 5-10 mM, 10-30 mM Glc, than the mannose 45% copolymer. However, the slope of mannose 45% copolymer is steeper in the area 30-100 mM and 100-500 mM Glc. This makes mannose 40% copolymer more sensitive in the area of 0-30 mM Glc and mannose 45% copolymer more sensitive in the area of 30-500 mM Glc.

Example 10

Sensor Formulation and Implantation

Fibres are made by dipping a glass rod of diameter 700 μm into a 15% w/w solution of polymer (1000PEGT80PBT20, application no. P9738GB) in dichloromethane and letting it dry at room temperature. This yields a hollow fibre of outer dimension 900 μm and lumen diameter 700 μm. The fibre is filled with the desired concentration of assay components [e.g. 5 μM of Alexa Fluor 594™-stained MBL (concentration stated with respect to the carbohydrate recognition domains) and 20 μM of HMCV1-stained amino-dextran 150 kDa]. Heating the polymer in order to melt it closes the ends of the fibre. The welded fibre is tested for leakage before testing and insertion.

This type of fibre can be placed in the top of the skin by the use of a needle. A needle of a suitable size (large enough to contain the wet fibre) is placed parallel to the skin surface at a depth of approximately 1 mm leaving the needle as a visible shadow through the skin. The fibre (still wet) is placed inside the needle and the needle is removed. Typically no bleeding is observed at the insertion site after the insertion procedure is completed.

When the fibre is in place the reading device is placed directly above the fibre and the measurements may begin. The glucose response may be measured by the use of time resolved fluorescence spectroscopy, corresponding to the response shown in FIG. 6.

Although the invention has been described with reference to preferred embodiments, it will be appreciated that various modifications are possible within the scope of the invention.

The invention claimed is:

1. A sensor for sensing analyte concentration, comprising at least two different variants of an appropriate competitive binding assay, the sensor being capable of sensing accurately a required range of analyte concentrations by means of the variants of the assay each being capable of sensing accurately a part only of the required range of analyte concentrations and the variants of the assay being chosen to sense overlapping or adjoining ranges of concentration covering the whole of the required range, wherein the competitive binding assays each comprise:
an analyte binding agent; and
an analyte analogue comprising at least one analyte analogue moiety;
wherein the analyte binding agent binds the at least one analyte analogue moiety of the analyte analogue to form a complex from which the analyte analogue is displaceable by said analyte; and
wherein the different assays are distinguished by the number or nature of the analyte analogue moieties comprised by the analyte analogue.

2. A sensor according to claim 1, wherein the analyte is carbohydrate.

3. A sensor according to claim 2, wherein the analyte is glucose.

4. A sensor according to claim 1, wherein the sensor produces a measurable optical response correlating to the analyte concentration.

5. A sensor according to claim 1, wherein the analyte binding agent is labelled with one of a proximity based signal generating/modulating moiety pair and the analyte analogue is labelled with the other of the proximity based signal generating/modulating moiety pair, and wherein there is a detectable difference in signal when the analyte analogue and analyte binding agent form the complex and when the analyte analogue is displaced by the analyte from the complex.

6. A sensor according to claim 1, wherein the analyte binding agent is a lectin.

7. A sensor according to claim 6, wherein the analyte binding agent is mannose binding lectin (MBL).

8. A sensor according to claim 1, wherein the at least one analyte analogue moiety is a carbohydrate or carbohydrate mimetic moiety.

9. A sensor according to claim 8, wherein the at least one analyte analogue moiety is a monosaccharide or oligosaccharide moiety.

10. A sensor according to claim 1, wherein the analyte analogue comprises a macromolecule.

11. A sensor according to claim 10, wherein the macromolecule is a protein, dendrimer, polysaccharide or synthetic polymer.

12. A sensor according to claim 11, wherein the macromolecule is a serum albumin.

13. A sensor according to claim 11, wherein the polysaccharide is derivatised to reduce the number of incorporated analyte analogue moieties.

14. A sensor according to claim 1, wherein in each competitive binding assay variant the analyte binding agent is MBL, the macromolecule is HSA and the analyte analogue moieties are mannose, and wherein each variant of the competitive binding assay contains an HSA-mannose conjugate comprising a different number of mannose moieties.

15. A sensor according to claim 1, wherein the analyte is glucose, and in each variant of the competitive binding assay the analyte binding agent is MBL and the macromolecule and analyte analogue moieties together form a derivatised dextran, and wherein each variant of the competitive binding assay contains a dextran derivatised such that the number of analyte analogue moieties incorporated into the dextran is different.

16. A sensor according to claim 15, wherein the sensor comprises two variants of a competitive binding assay, one variant being capable of sensing glucose concentrations in the range 0-10 mM, and the other variant being capable of sensing glucose concentrations in the range 0-25 mM.

17. A sensor according to claim 16, further comprising a third variant of a competitive binding assay, capable of sensing glucose concentrations in the range 15-40 mM.

18. A sensor according to claim 1, wherein the different variants of the assay are contained in separate compartments within the sensor.

19. A sensor according claim 1, wherein the sensor comprises at least two kinds of particles, each kind of particle containing a different variant of the competitive binding assay.

20. A sensor according to claim 18, wherein the material from which the particles or compartments are made is biodegradable.

21. A sensor according to claim 18, wherein the particles or compartments retain the components of the assay within a shell or matrix material.

22. A sensor according to claim 18, wherein the particles or compartments are permeable to the analyte and allow the analyte to freely diffuse into and out of the sensor and to contact the assay components, but are impermeable to the components of the variants of the competitive binding assay.

23. A method of using the sensor according to claim 1 in a living body, wherein: the sensor is implanted beneath the surface of the skin of the subject such that it is bathed in interstitial fluid; time is allowed for the analyte concentration in the interstitial fluid and in the sensor to equalise; light energy is supplied to the sensor;
an analyte concentration dependent fluorescence property of the assay is measured; the said measurement is converted into a readout of analyte concentration.

24. A method of using the sensor according to claim 1 in a living body, wherein: time is allowed for the analyte concentration to equalise in a sensor implanted beneath the surface of the skin of the subject and the interstitial fluid; light energy is supplied to the sensor; an analyte concentration dependent fluorescence property of the assay is measured; the said measurement is converted into a readout of analyte concentration.

* * * * *